(12) United States Patent
Melsky et al.

(10) Patent No.: US 8,540,704 B2
(45) Date of Patent: Sep. 24, 2013

(54) GUIDED CARDIAC ABLATION CATHETERS

(75) Inventors: Gerald Melsky, Lexington, MA (US);
Jeffrey M. Arnold, Wellesley, MA (US);
Edward L. Sinofsky, Dennis, MA (US);
Norman E. Farr, Monument Beach, MA (US)

(73) Assignee: CardioFocus, Inc., Marlborough, MA (US)

(*) Notice: Subject to any disclaimer, the term of this patent is extended or adjusted under 35 U.S.C. 154(b) by 1310 days.

(21) Appl. No.: 10/865,558

(22) Filed: Jun. 10, 2004

(65) Prior Publication Data

US 2005/0065504 A1    Mar. 24, 2005

Related U.S. Application Data

(63) Continuation-in-part of application No. 10/674,114, filed on Sep. 29, 2003, now Pat. No. 6,942,657, and a continuation-in-part of application No. 10/357,156, (Continued)

(51) Int. Cl.
*A61B 18/22* (2006.01)

(52) U.S. Cl.
USPC .................................. 606/15; 606/2

(58) Field of Classification Search
USPC .................... 606/2, 14–16, 32, 41
See application file for complete search history.

(56) References Cited

U.S. PATENT DOCUMENTS 3,417,745 A    12/1968 Sheldon
3,821,510 A    6/1974 Muncheryan (Continued)

FOREIGN PATENT DOCUMENTS

DE    94117543    11/1994
EP    0214712    3/1987

(Continued)

OTHER PUBLICATIONS

Bredikis, J. et al. "Laser Destruction of the Atrioventricular Bundle Using the Cardiac Endoscope" Kardiologiia, 1988, 28(8): 94-96.

(Continued)

*Primary Examiner* — Aaron Roane
(74) *Attorney, Agent, or Firm* — Leason Ellis LLP

(57) ABSTRACT

Guided ablation instruments are disclosed for creating lesions in tissue, especially cardiac tissue for treatment of arrhythmias, including atrial fibrillation. In one aspect of the invention, a percutaneous catheter is disclosed with an endoscope positionable in the instrument's distal end region to obtain an image. The image allows the clinician to determine whether contact has been achieved (or blood has been cleared from an ablative energy transmission path) before ablation begins or while ablation is occurring. In one embodiment, percutaneous ablation catheters are disclosed having at least one central lumen and one or more balloon structures at the distal end region of the instrument. Also disposed in the distal end region are an illuminating light source and an endoscope capable of collecting sufficient light to relay an image to the user. The instruments can further include an ablation element. The ablation element can be a contact ablation element, or a radiant energy emitter, which is preferably independently positionable within the lumen of the instrument and adapted to project ablative energy through a transmissive region of the instrument body (and/or balloon) to a target tissue site proximate to the pulmonary veins. The energy can delivered without the need for contact between the energy emitter and the target tissue so long as a clear transmission pathway is established. The endoscope element of the instrument allows the clinician to determine the position of the instrument and, if radiant energy is to be employed, see if such a pathway is clear. Moreover, because the position of the radiant energy emitter can be varied, endoscopic guidance permits the clinician to select a desired location and dose for the lesion.

29 Claims, 10 Drawing Sheets

Related U.S. Application Data filed on Feb. 3, 2003, now Pat. No. 8,025,661, which is a continuation-in-part of application No. 09/924,393, filed on Aug. 7, 2001, now Pat. No. 6,676,656, which is a continuation of application No. 09/616,275, filed on Jul. 14, 2000, now Pat. No. 6,626,900, which is a continuation-in-part of application No. 09/602,420, filed on Jun. 23, 2000, now Pat. No. 6,572,609, which is a continuation-in-part of application No. 09/357,355, filed on Jul. 14, 1999, now Pat. No. 6,423,055.

(60) Provisional application No. 60/477,374, filed on Jun. 10, 2003.

(56) References Cited

U.S. PATENT DOCUMENTS

| | | | |
|---|---|---|---|
| 4,224,929 | A | 9/1980 | Furihata |
| 4,233,493 | A | 11/1980 | Nath et al. |
| 4,273,109 | A | 6/1981 | Enderby |
| 4,336,809 | A | 6/1982 | Clark |
| 4,445,892 | A | 5/1984 | Hussein et al. |
| 4,585,298 | A | 4/1986 | Mori |
| 4,625,724 | A | 12/1986 | Suzuki et al. |
| 4,660,925 | A | 4/1987 | McCaughan, Jr. |
| 4,701,166 | A | 10/1987 | Groshong et al. |
| 4,718,417 | A | 1/1988 | Kittrell et al. |
| 4,770,653 | A | 9/1988 | Shturman |
| 4,781,681 | A | 11/1988 | Sharrow et al. |
| 4,819,632 | A | 4/1989 | Davies et al. |
| 4,842,390 | A | 6/1989 | Sottini et al. |
| 4,852,567 | A | 8/1989 | Sinofsky |
| 4,860,743 | A | 8/1989 | Abela |
| 4,862,886 | A | 9/1989 | Clarke et al. |
| 4,878,492 | A | 11/1989 | Sinofsky et al. |
| 4,878,725 | A | 11/1989 | Hessel et al. |
| 4,913,142 | A | 4/1990 | Kittrell et al. |
| 4,961,738 | A | 10/1990 | Mackin |
| 5,026,367 | A | 6/1991 | Leckrone et al. |
| 5,030,201 | A | 7/1991 | Palestrant |
| 5,053,033 | A | 10/1991 | Clarke |
| 5,071,417 | A | 12/1991 | Sinofsky |
| 5,078,681 | A | 1/1992 | Kawashima et al. |
| 5,090,959 | A | 2/1992 | Samson et al. |
| 5,109,859 | A | 5/1992 | Jenkins |
| 5,125,925 | A | 6/1992 | Lundahl |
| 5,133,709 | A | 7/1992 | Prince |
| 5,140,987 | A | 8/1992 | Schuger et al. |
| 5,151,096 | A | 9/1992 | Khoury |
| 5,151,097 | A | 9/1992 | Daikuzono et al. |
| 5,163,935 | A | 11/1992 | Black et al. |
| 5,169,395 | A | 12/1992 | Narciso, Jr. |
| 5,188,632 | A | 2/1993 | Goldenberg |
| 5,188,634 | A | 2/1993 | Hussein et al. |
| 5,190,538 | A | 3/1993 | Hussein et al. |
| 5,196,005 | A | 3/1993 | Doiron et al. |
| 5,207,699 | A | 5/1993 | Coe |
| 5,209,748 | A | 5/1993 | Daikuzono et al. |
| 5,219,346 | A | 6/1993 | Wagnieres et al. |
| 5,242,438 | A | 9/1993 | Saadatmanesh et al. |
| 5,261,904 | A | 11/1993 | Baker et al. |
| 5,269,777 | A | 12/1993 | Doiron et al. |
| RE34,544 | E | 2/1994 | Spears |
| 5,318,024 | A | 6/1994 | Kittrell et al. |
| 5,330,465 | A | 7/1994 | Doiron et al. |
| 5,337,381 | A | 8/1994 | Biswas et al. |
| 5,350,375 | A | 9/1994 | Deckelbaum et al. |
| 5,363,458 | A | 11/1994 | Pan et al. |
| 5,368,564 | A | 11/1994 | Savage |
| 5,374,953 | A | 12/1994 | Sasaki et al. |
| 5,380,316 | A | 1/1995 | Aita et al. |
| 5,380,317 | A | 1/1995 | Everett et al. |
| 5,395,362 | A | 3/1995 | Sacharoff et al. |
| 5,401,270 | A | 3/1995 | Muller et al. |
| 5,409,483 | A * | 4/1995 | Campbell et al. ............... 606/15 |
| 5,417,653 | A | 5/1995 | Sahota et al. |
| 5,418,649 | A * | 5/1995 | Igarashi ........................ 359/716 |
| 5,423,805 | A | 6/1995 | Brucker et al. |
| 5,427,119 | A | 6/1995 | Swartz et al. |
| 5,431,647 | A | 7/1995 | Purcell, Jr. et al. |
| 5,437,660 | A | 8/1995 | Johnson et al. |
| 5,441,497 | A | 8/1995 | Narciso, Jr. |
| 5,445,608 | A | 8/1995 | Chen et al. |
| 5,464,404 | A | 11/1995 | Abela et al. |
| 5,482,037 | A | 1/1996 | Borghi et al. |
| 5,496,305 | A | 3/1996 | Kittrell et al. |
| 5,497,774 | A | 3/1996 | Swartz et al. |
| 5,507,725 | A | 4/1996 | Savage et al. |
| 5,531,664 | A | 7/1996 | Adachi et al. |
| 5,536,265 | A | 7/1996 | van den Bergh et al. |
| 5,575,766 | A | 11/1996 | Swartz et al. |
| 5,605,162 | A | 2/1997 | Mirzaee et al. |
| 5,613,965 | A | 3/1997 | Muller |
| 5,643,253 | A | 7/1997 | Baxter et al. |
| 5,649,923 | A | 7/1997 | Gregory et al. |
| 5,662,712 | A | 9/1997 | Pathak et al. |
| 5,680,860 | A | 10/1997 | Imran |
| 5,690,611 | A | 11/1997 | Swartz et al. |
| 5,693,043 | A | 12/1997 | Kittrell et al. |
| 5,700,243 | A * | 12/1997 | Narciso, Jr. ............... 604/102.01 |
| 5,702,438 | A | 12/1997 | Avitall |
| 5,722,401 | A | 3/1998 | Pietroski et al. |
| 5,725,522 | A | 3/1998 | Sinofsky |
| 5,759,619 | A | 6/1998 | Jin et al. |
| 5,769,843 | A | 6/1998 | Abela et al. |
| 5,772,590 | A | 6/1998 | Webster, Jr. |
| 5,773,835 | A | 6/1998 | Sinofsky |
| 5,779,646 | A | 7/1998 | Koblish et al. |
| 5,782,239 | A | 7/1998 | Webster, Jr. |
| 5,782,899 | A | 7/1998 | Imran |
| 5,800,482 | A | 9/1998 | Pomeranz et al. |
| 5,807,395 | A | 9/1998 | Mulier et al. |
| 5,823,955 | A | 10/1998 | Kuck et al. |
| 5,824,005 | A | 10/1998 | Motamedi et al. |
| 5,830,209 | A | 11/1998 | Savage et al. |
| 5,833,682 | A | 11/1998 | Amplatz et al. |
| 5,843,073 | A | 12/1998 | Sinofsky |
| 5,845,646 | A | 12/1998 | Lemelson |
| 5,860,974 | A | 1/1999 | Abele |
| 5,885,278 | A | 3/1999 | Fleischman |
| 5,891,133 | A | 4/1999 | Murphy-Chutorian |
| 5,891,134 | A | 4/1999 | Goble et al. |
| 5,904,651 | A | 5/1999 | Swanson et al. |
| 5,908,415 | A | 6/1999 | Sinofsky |
| 5,931,834 | A | 8/1999 | Murphy-Chutorian et al. |
| 5,938,660 | A | 8/1999 | Swartz et al. |
| 5,947,959 | A | 9/1999 | Sinofsky |
| 5,967,984 | A * | 10/1999 | Chu et al. ..................... 600/439 |
| 5,971,983 | A | 10/1999 | Lesh |
| 5,995,875 | A | 11/1999 | Blewett et al. |
| 6,004,269 | A | 12/1999 | Crowley et al. |
| 6,012,457 | A | 1/2000 | Lesh |
| 6,024,740 | A | 2/2000 | Lesh et al. |
| 6,056,744 | A | 5/2000 | Edwards |
| 6,064,902 | A | 5/2000 | Haissaguerre et al. |
| 6,071,279 | A | 6/2000 | Whayne et al. |
| 6,071,281 | A | 6/2000 | Burnside et al. |
| 6,071,282 | A | 6/2000 | Fleischman |
| 6,071,302 | A | 6/2000 | Sinofsky et al. |
| 6,086,581 | A | 7/2000 | Reynolds et al. |
| 6,090,084 | A | 7/2000 | Hassett et al. |
| 6,099,514 | A | 8/2000 | Sharkey et al. |
| 6,102,905 | A | 8/2000 | Baxter et al. |
| 6,117,071 | A * | 9/2000 | Ito et al. ........................ 600/168 |
| 6,117,101 | A * | 9/2000 | Diederich et al. ............... 604/22 |
| 6,120,496 | A | 9/2000 | Whayne et al. |
| 6,146,379 | A | 11/2000 | Fleischman et al. |
| 6,159,203 | A | 12/2000 | Sinofsky |
| 6,161,543 | A | 12/2000 | Cox et al. |
| 6,164,283 | A | 12/2000 | Lesh |
| 6,179,835 | B1 | 1/2001 | Panescu et al. |
| 6,214,002 | B1 | 4/2001 | Fleischman et al. |
| 6,217,510 | B1 | 4/2001 | Ozawa et al. |
| 6,235,025 | B1 | 5/2001 | Swartz et al. |

| | | |
|---|---|---|
| 6,237,605 B1 | 5/2001 | Vaska et al. |
| 6,240,231 B1 | 5/2001 | Ferrera et al. |
| 6,245,064 B1 | 6/2001 | Lesh et al. |
| 6,251,092 B1 | 6/2001 | Qin et al. |
| 6,251,109 B1 | 6/2001 | Hassett et al. |
| 6,254,599 B1 | 7/2001 | Lesh et al. |
| 6,270,492 B1 | 8/2001 | Sinofsky |
| 6,305,378 B1 | 10/2001 | Lesh |
| 6,312,427 B1 | 11/2001 | Berube et al. |
| 6,314,962 B1 | 11/2001 | Vaska et al. |
| 6,325,797 B1 | 12/2001 | Stewart et al. |
| 6,352,531 B1 | 3/2002 | O'Connor et al. |
| 6,383,151 B1 | 5/2002 | Diederich et al. |
| 6,394,949 B1 | 5/2002 | Crowley et al. |
| 6,416,511 B1 | 7/2002 | Lesh et al. |
| 6,423,055 B1 | 7/2002 | Farr et al. |
| 6,423,058 B1 | 7/2002 | Edwards et al. |
| 6,471,697 B1 | 10/2002 | Lesh |
| 6,485,485 B1 | 11/2002 | Winston et al. |
| 6,500,174 B1 | 12/2002 | Maguire et al. |
| 6,502,576 B1 | 1/2003 | Lesh |
| 6,503,247 B2 | 1/2003 | Swartz et al. |
| 6,514,249 B1 | 2/2003 | Maguire et al. |
| 6,522,933 B2 | 2/2003 | Nguyen |
| 6,544,262 B2 | 4/2003 | Fleischman |
| 6,547,780 B1 | 4/2003 | Sinofsky |
| 6,554,794 B1 | 4/2003 | Mueller et al. |
| 6,558,375 B1 | 5/2003 | Sinofsky et al. |
| 6,562,020 B1 | 5/2003 | Constantz et al. |
| 6,572,609 B1 | 6/2003 | Farr et al. |
| 6,579,278 B1 | 6/2003 | Bencini |
| 6,579,285 B2 | 6/2003 | Sinofsky |
| 6,582,536 B2 | 6/2003 | Shimada |
| 6,605,055 B1 | 8/2003 | Sinofsky |
| 6,605,084 B2 | 8/2003 | Acker et al. |
| 6,626,900 B1 | 9/2003 | Sinofsky et al. |
| 6,635,054 B2 | 10/2003 | Fjield et al. |
| 6,648,875 B2 | 11/2003 | Simpson et al. |
| 6,669,655 B1 | 12/2003 | Acker et al. |
| 6,676,656 B2 | 1/2004 | Sinofsky |
| 6,679,873 B2 | 1/2004 | Rabiner et al. |
| 6,702,780 B1 | 3/2004 | Gilboa et al. |
| 6,771,996 B2 | 8/2004 | Bowe et al. |
| 6,896,673 B2 | 5/2005 | Hooven |
| 6,907,298 B2 | 6/2005 | Smits et al. |
| 6,916,306 B1 | 7/2005 | Jenkins et al. |
| 6,932,809 B2 | 8/2005 | Sinofsky |
| 6,942,657 B2 | 9/2005 | Sinofsky et al. |
| 6,953,457 B2 | 10/2005 | Farr et al. |
| 6,997,924 B2 | 2/2006 | Schwartz et al. |
| 7,207,984 B2 | 4/2007 | Farr et al. |
| 7,357,796 B2 | 4/2008 | Farr et al. |
| 7,935,108 B2 | 5/2011 | Baxter et al. |
| 8,025,661 B2 | 9/2011 | Arnold et al. |
| 2001/0030107 A1 | 10/2001 | Simpson |
| 2002/0019627 A1 | 2/2002 | Maguire et al. |
| 2002/0029062 A1 | 3/2002 | Satake |
| 2002/0065512 A1 | 5/2002 | Fjield et al. |
| 2002/0091383 A1 | 7/2002 | Hooven |
| 2002/0107511 A1 | 8/2002 | Collins et al. |
| 2002/0115995 A1 | 8/2002 | Lesh et al. |
| 2002/0120264 A1 | 8/2002 | Crowley et al. |
| 2002/0183729 A1 | 12/2002 | Farr et al. |
| 2002/0183739 A1 | 12/2002 | Long |
| 2003/0050632 A1 | 3/2003 | Fjield et al. |
| 2003/0065307 A1 | 4/2003 | Lesh |
| 2003/0069620 A1 | 4/2003 | Li |
| 2003/0111085 A1 | 6/2003 | Lesh |
| 2003/0120270 A1 | 6/2003 | Acker |
| 2003/0144657 A1 | 7/2003 | Bowe et al. |
| 2003/0158550 A1 | 8/2003 | Ganz et al. |
| 2003/0171746 A1 | 9/2003 | Fleischman |
| 2004/0006333 A1 | 1/2004 | Arnold et al. |
| 2004/0054360 A1 | 3/2004 | Schwartz et al. |
| 2004/0059397 A1 | 3/2004 | Sinofsky et al. |
| 2004/0122290 A1 | 6/2004 | Irion et al. |
| 2005/0038419 A9 | 2/2005 | Arnold et al. |
| 2005/0065504 A1 | 3/2005 | Melsky et al. |
| 2005/0222558 A1 | 10/2005 | Baxter et al. |
| 2005/0234436 A1 | 10/2005 | Baxter et al. |
| 2005/0288654 A1 | 12/2005 | Nieman et al. |
| 2006/0253113 A1 | 11/2006 | Arnold et al. |
| 2007/0078451 A1 | 4/2007 | Arnold et al. |
| 2008/0039746 A1 | 2/2008 | Hissong et al. |
| 2008/0108870 A1 | 5/2008 | Wiita et al. |
| 2008/0195088 A1 | 8/2008 | Farr et al. |
| 2009/0221996 A1 | 9/2009 | Lesh et al. |
| 2009/0221997 A1 | 9/2009 | Arnold et al. |
| 2009/0275934 A1 | 11/2009 | Baxter et al. |
| 2009/0299354 A1 | 12/2009 | Melsky et al. |
| 2009/0326320 A1 | 12/2009 | Sinofsky et al. |
| 2011/0082449 A1 | 4/2011 | Melsky et al. |
| 2011/0082450 A1 | 4/2011 | Melsky et al. |
| 2011/0082451 A1 | 4/2011 | Melsky |
| 2011/0082452 A1 | 4/2011 | Melsky et al. |
| 2011/0245822 A1 | 10/2011 | Baxter et al. |
| 2011/0245828 A1 | 10/2011 | Baxter et al. |

FOREIGN PATENT DOCUMENTS

| | | |
|---|---|---|
| EP | 0292621 | 11/1988 |
| EP | 0292695 | 11/1988 |
| EP | 0299448 | 1/1989 |
| EP | 0311458 | 4/1989 |
| EP | 0437181 | 7/1991 |
| EP | 0437183 | 7/1991 |
| EP | 0439629 | 8/1991 |
| EP | 0598984 | 6/1994 |
| EP | 0792664 | 9/1997 |
| EP | 1072231 | 1/2001 |
| EP | 1331893 | 12/2004 |
| FR | 2798371 A | 3/2001 |
| JP | 2003-210028 A | 7/2003 |
| JP | 2004-065076 A | 3/2004 |
| WO | WO 9217243 | 10/1992 |
| WO | WO 9306888 | 4/1993 |
| WO | WO 9319680 | 10/1993 |
| WO | WO 9325155 | 12/1993 |
| WO | WO 9417434 | 8/1994 |
| WO | WO 9426184 | 11/1994 |
| WO | WO 9607451 | 3/1996 |
| WO | WO 9634646 | 11/1996 |
| WO | WO 9640342 | 12/1996 |
| WO | WO 9737714 | 10/1997 |
| WO | WO 00/67832 | 11/2000 |
| WO | WO 01/03599 A2 | 1/2001 |
| WO | WO 0113812 | 3/2001 |
| WO | WO 01/64123 | 9/2001 |
| WO | WO 02/096479 | 12/2002 |
| WO | WO 03090835 | 11/2003 |
| WO | WO 2004-110258 | 12/2004 |

OTHER PUBLICATIONS

Chevalier, P. et al. "Thoracoscopic Epicardial Radiofrequency Ablation for Vagal Atrial Fibrillation in Dogs" PACE, 1999, 22: 880-886.

Froelich, J. et al. "Evaluation of a Prototype Steerable Angioscopic Laser Catheter in a Canine Model: A Feasibility Study" Cardiovasc Intervent Radiol, 1993 16: 235-238.

Fujimura, O. et al. "Direct In Vivo Visualization of Right Cardiac Anatomy by Fiberoptic Endoscopy" Angiology; 1995, 46 (3): 201-208.

Fujimura, O. et al. "Direct In Vivo Visualization of Right Cardiac Anatomy by Fiberoptic Endoscopy: Observation of Radiofrequency-Induced Acute Lesions Around the Ostium of the Coronary Sinus" European Heart J., 1994, 15: 534-540.

Gamble, W. and Innis, R. "Experimental Intracardiac Visualization" NEJM, 1967, 276(25): 1397-1403.

Hirao, K. et al. "Transcatheter Neodymium-Yttrium-Aluminum-Garnet Laser Coagulation of Canine Ventricle Using a Balloon-Tipped Cardioscope" Jpn Circ J., 1997, 61: 695-703.

Keane, D. et al. "Pulmonary Vein Isolation for Atrial Fibrillation" Rev Cardiovasc Med., 2002, 3(4): 167-175.

Kuo, C. et al. "In Vivo Angioscopic Visualization of Right Heart Structure in Dogs by Means of a Balloon-Tipped Fiberoptic Endoscope: Potential Role in Percutaneous Ablative Procedures." American Heart J., 1994, 127: 187-197.

Nakagawa, H. et al. "Cardioscopic Catheter Ablation with Noncontact, Pulsed Nd:YAG Laser Using Saline Inflated Balloon Catheter," Presentation JACC 1998; 31: 118A-119A.

Obelienius, V. et al. "Transvenous Ablation of the Atrioventricular Conduction System by Laser Irradiation Under Endoscopic Control" Lasers in Surgery Medicine, 1985, 5: 469-474.

Roggan, A., et al. "Optical Properties of Circulating Human Blood in the Wavelength Range 400-2400 nm" J Biomedical Optics, 1999, 4(1): 36-46.

Saliba, W. et al. "Circumferential Ultrasound Ablation for Pulmonary Vein Isolation: Analysis of Acute and Chronic Failures" J Cardiovascular Electrophysiology, 2002, 13(10): 957-961.

Shure, D. et al. "Identification of Pulmonary Emboli in the Dog: Comparison of Angioscopy and Perfusion Scanning" Circulation, 1981, 64(3): 618-621.

Shure, D., et al. "Fiberoptic Angioscopy: Role in the Diagnosis of Chronic Pulmonary Arterial Obstruction" Ann Int Med., 1985, 103: 844-850.

Tanabe, T. et al. "Cardiovascular Fiberoptic Endoscopy: Development and Clinical Application" Surgery, 1980, 87(4): 375-379.

Tanaka, K. et al., "Endoscopy-Assisted Radiofrequency Ablation Around the Coronary Sinus Ostium in Dogs: Its Effects on Atrioventricular Nodal Properties and Ventricular Response During Atrial Fibrillation," Journal of Cardiovascular Electrophysiology, vol. 7, No. 11, Nov. 1996, pp. 1063-1073.

Uchida, Y. et al. "Fiberoptic Angioscopy of Cardiac Chambers, Valves, and Great Vessels Using a Guiding Balloon Catheter in Dogs." American Heart J., 1998, 115(6): 1297-1302.

Uchida, Y. et al. "Percutaneous Pulmonary Angioscopy Using a Guiding Balloon Catheter" Clin. Cardiol., 1988, 11: 143-148.

Vanermen, H. et al. "Minimally Invasive Video-Assisted Mitral Valve Surgery: From Port-Access Towards a Totally Endoscopic Procedure" J Card Surg., 2000, 15: 51-60.

Yamamoto, N et al. "Nonfluoroscopic Guidance for Catheter Placement into the Coronary Sinus under Direct Vision Using a Balloon-Tipped Cardioscope" PACE, 1998; 21: 1724-1729.

* cited by examiner

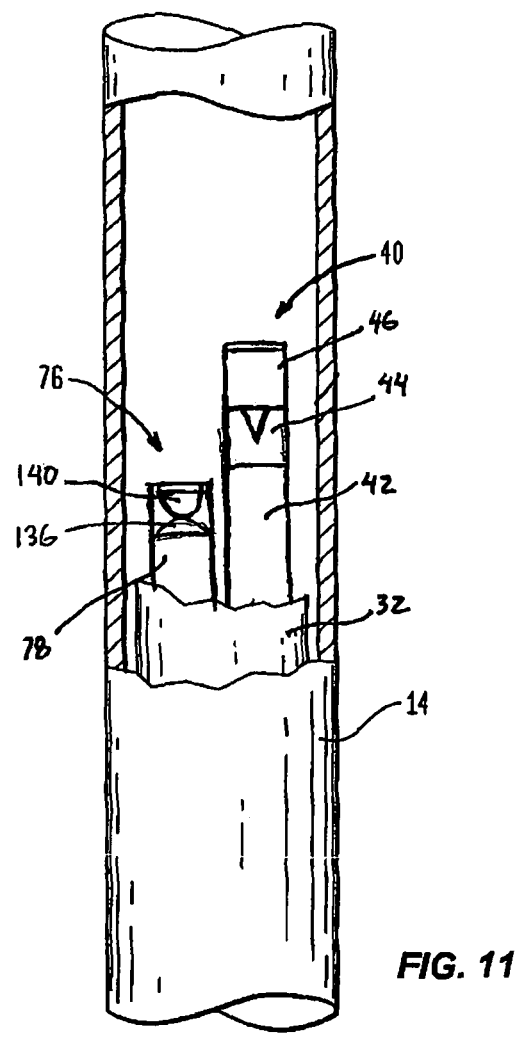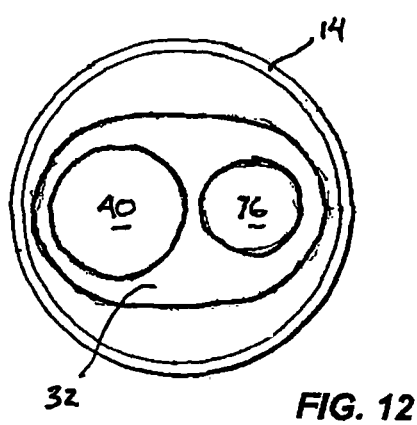
FIG. 11
FIG. 12

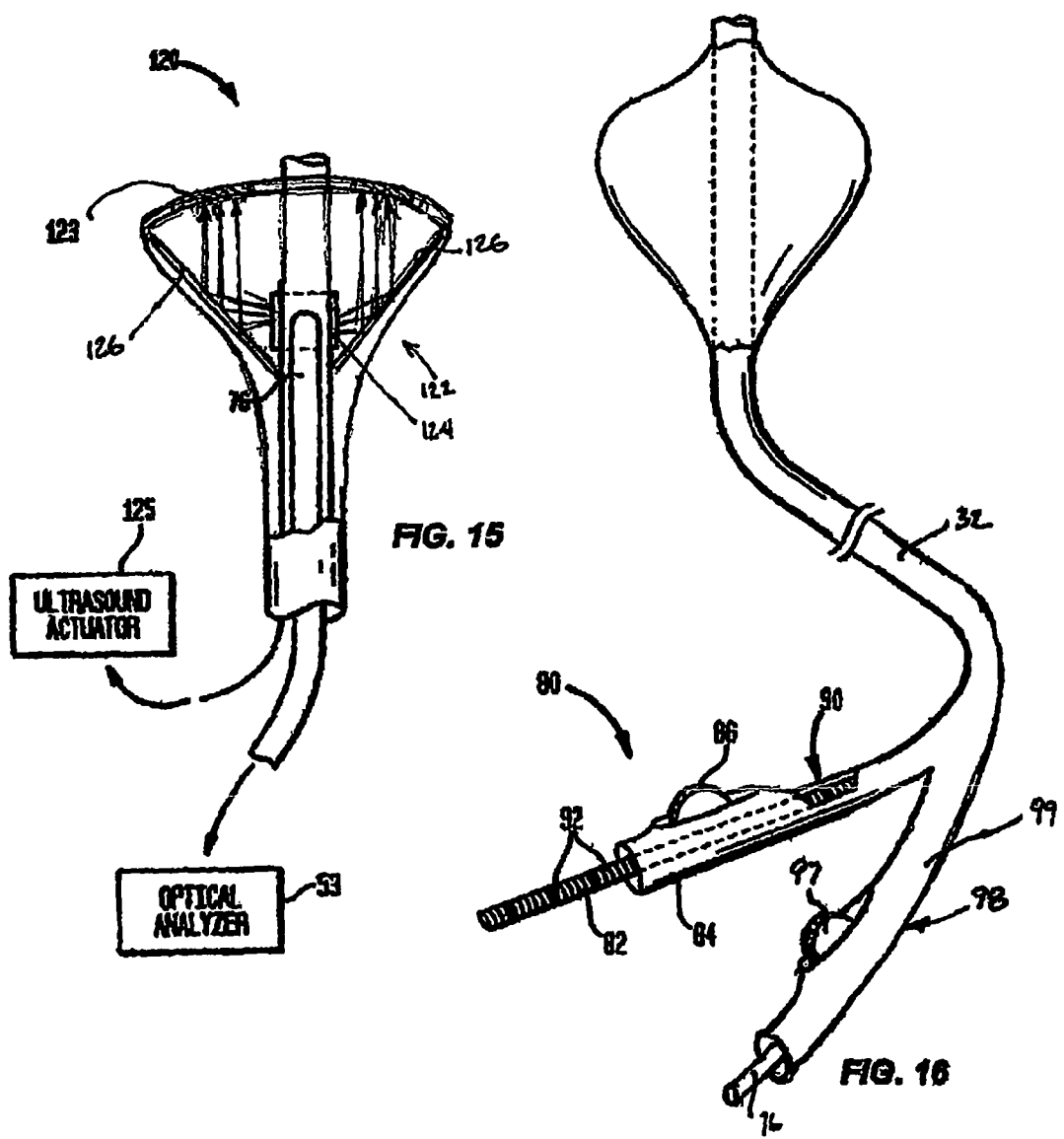

GUIDED CARDIAC ABLATION CATHETERS

CROSS-REFERENCE TO RELATED APPLICATIONS

This application claims priority of U.S. Provisional Patent Application Ser. No. 60/477,374, filed Jun. 10, 2003.

This application is a continuation-in part of U.S. patent application Ser. No. 10/357,156, filed Feb. 3, 2003, which is a continuation-in-part of U.S. patent application Ser. No. 09/924,393, filed on Aug. 7, 2001.

This application is also a continuation-in-part of U.S. patent application Ser. No. 10/674,114, filed Sep. 29, 2003, which is a continuation of U.S. patent application Ser. No. 09/616,275 filed Jul. 14, 2000, now U.S. Pat. No. 6,626,900, which is a continuation-in-part of U.S. patent application Ser. No. 09/602,420 filed Jun. 23, 2000, now U.S. Pat. No. 6,572,609, which is a continuation-in-part of U.S. patent application Ser. No. 09/357,355, filed on Jul. 14, 1999, now U.S. Pat. No. 6,423,055 issued Jul. 22, 2002.

The teachings of all of these prior related applications are hereby expressly incorporated by reference.

BACKGROUND OF THE INVENTION

The present invention relates to ablation instruments for the treatment of atrial fibrillation and, in particular, to percutaneous instruments employing energy emitters for the ablation of tissue surrounding the pulmonary veins. Methods of ablating tissue to treat atrial fibrillation using radiant energy are also disclosed.

Atrial fibrillation is the most common cardiac arrhythmia and affects approximately 2.3 million people in the United States. It is characterized by rapid randomized contractions of atrial myocardium, causing an irregular, often rapid ventricular rate. The regular pumping function of the atria is replaced by a disorganized, ineffective quivering as a result of chaotic conduction of electrical signals through the upper chambers of the heart. Weakness, lightheadedness, fainting, heart failure, stroke and even death can result.

In 1991, Dr. James Cox developed a surgical procedure, called the Maze Procedure, to cure atrial fibrillation, It involved cutting the atrial wall into many pieces in an intricate pattern and sewing them back together. The scar tissue that formed blocked the conduction of electrical impulses and caused them to follow a pre-arranged pattern. Although this procedure was successful in curing atrial fibrillation, the difficulty of the procedure, its invasive nature and the morbidity involved prevented its widespread adoption.

Prior to the late 1990's it was believed that less invasive procedures and associated devices to cure atrial fibrillation would have to mimic the Maze procedure and create long lines of conduction block in the atrial wall. Several types of ablation devices were proposed which utilized some form of energy, generally radio-frequency ("RF") heating to create elongated lesions that extend through a sufficient thickness of the myocardium to block electrical conduction. Many of the proposed ablation instruments are percutaneous devices that are designed to create such lesions from within the heart. Such devices are positioned in the heart by catheterization of the patient, e.g., by passing the ablation instrument into the heart via a blood vessel, such as the femoral vein. See, for example, U.S. Pat. No. 5,575,766 issued to Swartz, which discloses the use of ablation electrodes introduced into the heart via a catheter to create Maze-like lesions and U.S. Pat. No. 5,904,651 issued to Swanson, which discloses a similar electrical ablation device with an imaging element to create Maze-like lesions under visual control. However, because of the difficulty in creating long lesions that were correctly located, continuous and transmural (through the heart wall) these devices have not achieved clinical or commercial success.

In 1997 and 1998 two seminal papers by Drs. Jais and Hassaguerre identified the pulmonary veins as the primary origin of errant electrical signals responsible for triggering atrial fibrillation. By ablating the heart tissue at selected locations in or surrounding the pulmonary veins, electrical impulses from such foci of fibrillation can be blocked. In one known approach, circumferential ablation of tissue within the pulmonary veins, at the ostia (mouth) of such veins or outside of the veins has been practiced to treat atrial fibrillation. Similarly, ablation of the region surrounding the pulmonary veins as a group has also been proposed.

Several types of catheter ablation devices have recently been proposed for creating circumferential lesions to treat atrial fibrillation, including devices which employ radio-frequency, microwave or ultrasonic energy or cryogenic cooling. Regardless of the type of ablation instrument used, the desired result is a continuous circumferential lesion that isolates the foci that trigger fibrillation from the atrial tissue. Post-ablation electrical mapping is usually necessary to determine whether a circumferential lesion has been formed. If electrical conduction is still present, the encircling lesion is incomplete and the procedure must be repeated or abandoned.

Generally for the ablation instrument to be effective a clear transmission pathway is desired, e.g., a pathway from which blood has been substantially cleared. If there is too much blood between the ablation element and the target tissue, the ablation energy will be attenuated and the lesion will not be continuous and block electrical conduction.

One way to limit the amount of blood between the ablation element and the tissue is to force the ablation instrument deeper in the vein. However, if the energy application is too deep in the vein, it can result in damage to the vein and resultant narrowing of the vein, called pulmonary vein stenosis, which has serious consequences and can be life threatening.

The correct positioning of the ablation device in the heart to obtain complete lesions that will provide conduction block without damaging sensitive tissues is complicated by the fact that the standard imaging technique available to the physician for the procedure is x-ray fluoroscopy which does a poor job of imaging soft tissues such as the heart and pulmonary veins. X-ray contrast injection can be used to aid in imaging smaller arteries such as the coronary arteries but such injection is of very limited use when the entire heart or vessels as large as the pulmonary veins need to be imaged. As a result, the physician using these ablation catheters has limited ability to understand the detailed anatomy of the vein and to understand how the ablation catheter is positioned in that anatomy.

Existing instruments for cardiac ablation suffer from a variety of design limitations. In one common approach, described, for example, in U.S. Pat. No. 6,012,457 issued to Lesh on Jan. 11, 2000 and in International Application Pub. No. WO 00/67656 assigned to Atrionix, Inc, a guide wire or similar guide device is advanced through the left atrium of the heart and into a pulmonary vein. A catheter instrument with an expandable element is then advanced over the guide and into the pulmonary vein where the expandable element (e.g., a balloon) is inflated. The balloon structure also includes a circumferential ablation element, e.g., an RF electrode carried on the outer surface of the balloon, which performs the ablation procedure. In order for the electrode to be effective, it must in contact with the tissue throughout the procedure. In such devices, a major limitation in prior art percutaneous designs is their inability to maintain such contact with the actual and quite varied geometry of the heart. The inner surface of the atrium is not regular. In particular, the mouths of the pulmonary veins do not exhibit regularity; they often bear little resemblance to conical or funnel-shaped openings. When the expandable, contact heating devices of the prior art encounter irregularly-shaped ostia, the result can be an incompletely formed (non-circumferential) lesion. This limitation is also present in the case of cryogenic balloon catheters where contact with the target tissue is required in order to perform the desire lesion.

Another problem commonly encountered in maneuvering an instrument within the left atrium is the need to detect side branches in the pulmonary veins. If the energy is delivered into a side branch a lesion will not be formed at that location and a circumferential lesion will not be formed. A related problem is that it is often difficult to distinguish between blood at the target site, which can sometimes be remedied by reseating of the instrument, and the presence of a vessel side branch, which will preclude formation of a continuous lesion regardless of attempts to reseat at the location. This problem is underscored by a study by Saliba et al., *Journal of Cardiovascular Electrophysiology*, Vol. 13, No. 10, pp. 957-961 Oct. 12, 2002, in which the authors report a success rate of only 39% in treating atrial fibrillation in 33 patients using a circumferential ultrasound ablation device. Among the causes for failure of the device suggested by the authors were eccentric balloon placement in the pulmonary vein and inability to detect early branching of the vein which would result in ineffective circumferential energy delivery.

Another limitation in the prior art percutaneous designs is the lack of site selectability. Practically speaking, each prior art percutaneous instrument is inherently limited by its design to forming an ablative lesion at one and only one location. For example, when an expandable balloon carrying an RF heating surface on it surface is deployed at the mouth of a vein, the lesion can only be formed at a location defined by the geometry of the device. It is not possible to form the lesion at another location because the heating element must contact the target tissue. If the ablation element is not in contact with tissue at some location the entire catheter must be repositioned in an attempt to obtain contact. Often it is not possible to find a single position where contact is obtained completely around the vein.

U.S. Pat. No. 6,514,249 issued to Maguire et al. on Feb. 4, 2003 discloses one approach to positioning an ablation element within a pulmonary vein ostium. This patent describes the use of ultrasound, pressure or temperature sensors to determine if the instrument is in contact with a target region of tissue. While such sensors can be useful in determining contact at a particular location, the devices disclosed by U.S. Pat. No. 6,514,249 can not provide an image of the anatomy of the vein, the location of side branches or the position of the instrument relative to the target site in a manner that would allow a clinician to devise an optimal ablation plan.

Accordingly, there is a need for better ablation instruments that can form lesions with less trauma to the healthy tissue of the heart and provide a greater likelihood of successfully producing fully circumferential lesions. A percutaneous system that can aid in visualizing the anatomy of the vein, in determining the location of side branches, in visualizing the position of the catheter relative to the vein and any side branches, in determining whether contact has been achieved (or blood has been cleared from an ablative energy transmission path) before ablation, and in determining the optimum location for energy delivery would improve the likelihood of first-time success based on such determinations and would represent a significant improvement over the existing designs.

Moreover, a percutaneous ablation device that allowed the clinician to select the location of the ablation site based upon such visualization would be highly desirable. One such device is described in commonly-owned, parent applications, e.g., U.S. patent application Ser. No. 10/357,156, filed Feb. 3, 2003 and Ser. No. 09/924,393, filed on Aug. 7, 2001, which disclose a balloon ablation device having an energy emitting element and an optical sensor. The energy emitting element is independently positionable within the lumen of the instrument and adapted to project ablative energy through a transmissive region of a balloon to a target tissue site.

Because the position of the radiant energy emitter can be varied, the clinician can select the location of the desired lesion without the necessity of repositioning the instrument. Applicants' basic devices, as described in the prior filings, thus, allow a clinician to choose from a number of different lesion locations and, if desired, also permit the formation of composite lesions that combine to form continuous conduction blocks around pulmonary veins or other cardiac structures.

However, even Applicants' advanced ablation devices could benefit from enhanced visualization of the cardiac anatomy. Similarly, any sophisticated cardiac ablation device could likewise benefit from visual data in instrument positioning, identifying targets, and/or monitoring the progress of ablative procedures as well as selecting an optimal dose based on the location to be treated.

SUMMARY OF THE INVENTION

Guided ablation instruments are disclosed for creating lesions in tissue, especially cardiac tissue for treatment of arrhythmias and the like. In one aspect of the invention, a percutaneous catheter is disclosed with an endoscope positionable in the instrument's distal end region to obtain an image. The image allows the clinician to visualize the anatomy of the vein, the location of side branches and the position of the instrument relative to the vein. The clinician can determine whether contact has been achieved (or blood has been cleared from an ablative energy transmission path) and the optimum location for ablation or radiation dosing before ablation begins or while ablation is occurring.

In one embodiment, percutaneous ablation catheters are disclosed having at least one central lumen and one or more balloon structures at the distal end region of the instrument. Also disposed in the distal end region is an illuminating light source and an endoscope capable of collecting sufficient light to relay an image to the user. The instruments can further include an energy emitting element, which is preferably independently positionable within the lumen of the instrument (e.g., along a longitudinal axis of the balloon) and adapted to project ablative energy through a transmissive region of the instrument body (and/or balloon) to a target tissue site. The energy can be delivered without the need for contact between the energy emitter and the target tissue so long as a clear transmission pathway is established. The endoscope element of the instrument allows the clinician to see if such a pathway is clear.

Moreover, when the position of the radiant energy emitter can be varied, endoscopic guidance permits the clinician to select a desired location and dose for the lesion. Endoscopic inspection thus permits the clinician to define a priori an "ablation plan" before performing ablation. Based on the location and size of the lesion, the present inventions permits the user to select a suitable energy level, e.g., to compensate for the power changes due to the size of the lesion and/or to compensate for the amount of attenuation caused by projecting energy to a target site across a greater distance.

In another aspect of the invention, generally applicable to a wide range of cardiac ablation instruments, mechanisms are disclosed for determining whether the instrument has been properly seated within the heart, e.g., whether the device is in contact with a pulmonary vein and/or the atrial surface, in order to form a lesion by heating, cooling or projecting energy. The projected energy can be focused by either refractive or reflective elements. This contact-sensing feature can be implemented by an illumination source and an endoscope situated within the instrument. The image captured by the endoscope from the reflected light can be used to determine whether contact has been achieved and whether such contact is continuous over a desired ablation path. The image data can also be enhanced by selective wavelength capture, optical filtering, or other image data processing techniques.

Monitoring allows the clinician to observe balloon inflation and establish an optimal size (with sufficient contact for ablation). Reflective monitoring and/or imaging, especially with wide field of view optics, can be used to determine if the instrument is too deep within a pulmonary vein by mapping tissue contact on the balloon. For example, tissue contact with proximal (rear) portions of the balloon can indicate over-insertion of the balloon in to a vein. Because the device has a wide angle field of view and a large depth of field the clinician can also see the relationship of the balloon to the pulmonary vein ostia. This capability allows the clinician to determine if the balloon is too deep in the pulmonary vein because the optical sensor has the ability to see a large portion of the interior the balloon. Any tissue contact determined to be proximal to the apex (widest segment) of the balloon would indicate that the instrument is too deep in the vein and has the possibility of causing pulmonary vein stenosis.

In addition, because inflation of the balloon can be observed under direct visualization, the clinician can determine it the balloon is stretching the vein radially by assessing if full contact is achieved before the balloon is completely inflated. This stretching condition would also indicate that the balloon is too distal in the pulmonary vein and could cause damage.

In order to determine if there is tissue contact with the proximal portion of the balloon, the endoscope needs to have a wide field of view. In one preferred embodiment, the endoscope can have a field of view greater than about 70 degrees, preferably greater than 90 degrees. In addition, to see the back of the balloon, as well as the front of the balloon. the endoscope can be placed in the back of the balloon as well as possess a long depth of field. The endoscope's depth of field can be greater than 13 mm, preferably greater than 25 mm, and more preferably, in some applications, greater than 35 mm. The f-number of the endoscope can be less than 4, preferably less than 3 and more preferably less than 2.5.

When used in conjunction with a radiant energy emitter, the endoscope and ablation element can be introduced as an assembly. In such configurations, the energy emitter can also serve as the illumination source by operating at a low power level to provide the light for image acquisition. Alternatively, either the endoscope or the ablative element (or both) can be independently positionable within the instrument.

Endoscopic guidance has several advantages over conventional guidance or location systems. For example, fluoroscopic location techniques offer at best a two-dimensional view of a percutaneous cardiac instrument vis-à-vis heart structures. Such two-dimensional views can be deceiving and the fluoroscopic images of veins during dye injection are transient, at best. In addition, contrast medium flowing through a vein can not reliably detect side branches or permit imaging of the heart itself. Moreover, fluoroscopic images are ill-suited for determining whether a balloon structure has been seated in contact with a tissue structure, e.g., a pulmonary vein ostium. Ultrasound images are likewise limited in their ability to ascertain tissue contact. The endoscopic guidance apparatus and methods of the present invention readily permit instruction location with a high degree of accuracy and also provide a simple, well defined measurement of the degree of circumferential contact between an instrument e.g., a projection balloon surface and target tissue. In one embodiment, the endoscope can be in a fixed position relative to the projection balloon.

In addition to determining the degree of contact between the instrument and the tissue, the endoscope can be used to determine the extent of tissue ablation by sensing the change in color of the tissue as it is ablated. Moreover, the endoscope can be used to detect the formation of potentially dangerous coagulated blood at the site of ablation and to allow the clinician to terminate the ablation if necessary for safety reasons. The endoscopic image can also be used to extract colorimetric data, e.g., to distinguish between tissue and blood.

In a further embodiment of the invention, a cardiac ablation instrument is disclosed having an elongate catheter body with a distal portion adapted for disposition within a heart. This catheter body has at least one lumen therein and an expandable, energy-transmitting element which can be deployed at the desired location with or without an anchorage element to contact a cardiac structure and establish a transmission pathway. For example, the expandable element can be a projection balloon that is expandable to fill the space between the energy emitter and the target tissue with an energy-transmissive fluid and, thereby, provide a transmission pathway for projected radiant energy. The balloon can further be used to collapse trabecular tissue and, thereby, define a focal region into which a uniform dose of ablative energy can be projected or reflected. More generally, the balloon can be used to smooth irregular tissue surfaces and/or define focal planes or curved focal surfaces for the delivery of ablative energy to cardiac tissue in contact with such surfaces. The instrument can further include a radiant energy delivery element movable within the lumen of the catheter body such that it can be disposed at the desired location and deliver radiant energy through a transmissive region of the instrument to a target tissue site. The movable energy emitter thus permits multi-step treatments, e.g., encircling an asymmetric vein structure with a series of arc-shaped lesions, without the need for repositioning of the balloon or any other portion of the instrument. The instrument can further include additional elements, such fluid delivery ports, to provide a blood-free transmission pathway from the energy emitter to the tissue target. In accordance with the invention, an endoscope is disposed within the projection balloon to monitor and/or guide instrument placement.

Mechanisms are disclosed for determining whether the ablation instruments of the present invention have been properly seated within the heart to form a lesion. For example, if a projection balloon is employed to provide a clear transmission pathway from a radiant energy emitter to the target tissue, the mechanisms of the present invention can sense by endoscopic imaging whether contact has been achieved between the balloon and the target tissue (and/or whether the pathway for projection of radiant energy has been otherwise cleared of blood). In one embodiment, this contact-sensing feature can be implemented by an illumination fiber situated within the instrument and an imaging fiber assembly that collects reflected light. Images obtained by capture of reflected light (or particular wavelengths of the reflected light) can thus be used to determine whether contact has been achieved between the projection balloon and the target tissue, whether blood has been cleared from any gaps and whether a clear and continuous transmission pathway has been established over a desired ablation path.

In a further aspect of the invention, percutaneous instruments are disclosed that can achieve rapid and effective coagulation or ablation through the use of tissue-penetrating radiant energy. It has been discovered that radiant energy, e.g., projected electromagnetic radiation or ultrasound, can create lesions in less time and with less risk of the adverse types of surface tissue destruction commonly associated with prior art approaches. Unlike instruments that rely on thermal conduction or resistive heating, controlled penetrating radiant energy can be used to simultaneously deposit energy throughout the full thickness of a target tissue, such as a heart wall. Radiant energy can also produce better defined and more uniform lesions. The extent of lesion formation can also be monitored in real-time by the endoscopic imaging and used in a feedback control mode to control the duration of ablation and/or induce modifications of the ablation protocol to achieve a desired or optimized result.

The use of radiant energy, in conjunction with catheter structures that are substantially transparent to such radiation at the therapeutic wavelengths, is particularly advantageous in affording greater freedom in selecting the location of the lesion, e.g., the site is no longer limited to the pulmonary vein itself. Because the energy can be projected onto the tissue, a ring-like lesion can be formed in atrial tissue at a distance from the vein, thereby reducing the potential for stenosis and/or other damage to the vein itself. Endoscopic-guidance allows the clinician to select a desired lesion location and implement a desired ablation plan by appropriate placement of the radiant energy emitter.

In certain embodiments, infrared radiation is particularly useful in forming photoablative lesions. In certain preferred embodiments, the instruments emit radiation at a wavelength in a range from about 800 nm to about 1000 nm, and preferably emit at a wavelength in a range of about 915 nm to about 980 nm. Radiation at a wavelength of 915 nm or 980 nm is commonly preferred, in some applications, because of the optimal absorption of infrared radiation by cardiac tissue at these wavelengths. Such infrared radiation can also be useful as illumination light for the endoscope when provided at a sufficiently low power to capture images without untoward damage to the image capture elements of the invention. Alternatively, ablation can be performed with infrared radiation while one or more white light sources can serve as the illumination component.

In another embodiment, focused ultrasound energy can be used to ablate cardiac tissue. In certain preferred embodiments, an ultrasound transducer can be employed to transmit frequencies within the range of about 5 to about 20 MHz, and preferably in some applications within the range of about 7 MHz to about 10 MHz. In addition, the ultrasonic emitter can include focusing and/or reflective elements to shape the emitted energy into an annular beam or other desired shape.

However, in certain applications, other forms of radiant energy can also be useful including, but not limited to, other wavelengths of light, other frequencies of ultrasound, x-rays, gamma-rays, microwave radiation and hypersound.

In the case of radiant light, the energy delivering element can include a light transmitting optical fiber adapted to receive ablative radiation from a radiation source and a light emitting tip at a distal end of the fiber for emitting radiation. The light delivering element can be slidably disposed within an inner lumen of the catheter body and the instrument can further include a translatory mechanism for disposing the tip of the light delivering element at one or more of a plurality of locations with the catheter. Moreover, by moving the energy-projecting tip assembly within the catheter, the diameter of the projected ring or arc of energy can be readily varied, thereby permitting the clinician control over the location (and size) of the lesion to be formed. Endoscopic guidance not only permits determinations of location but also the extent of tissue contact in such systems and facilitates accurate dosimetry calculations for lesions of variable size.

The present invention provides mechanisms for visualizing where the energy will be applied prior to treatment. In one embodiment, the energy delivering element can include an aiming light source to project visible light onto the tissue, and reflected light can be observed via the endoscope. This visible light from the aiming beam provides an indication to the clinician of the exact location of energy delivery. Markers on the balloon are also disclosed for such visualization based on known correlations between the variable position of the energy source and particular regions of the balloon. In another embodiment, virtual markers are employed. Based on such visual data, the location of ablation element can be selected to optimize the lesion formed upon activation of the ablation element.

Optionally, a fluid can be disposable between the radiant energy delivery element and the target region. In one preferred embodiment a "projection balloon" is filled with a radiation-transmissive fluid so that radiant energy from the energy emitter can be efficiently passed through the instrument to the target region. The fluid can also be used to cool the energy emitter through conduction or via a closed or open circulator system. In certain applications, it can be desirable to used deuterium oxide (so-called "heavy water") as a balloon-filling fluid medium because of its loss absorption characteristics vis-à-vis infrared radiation. In other applications, the inflation fluid can be water or saline or an admixture of such fluids with deuterium oxide (to enhance ablative energy transmission) and/or sodium diatrazoate (to enhance radiographic imaging).

It can also be desirable to employ an "ablative fluid" outside of the instrument (e.g., between the balloon and the target region) to ensure efficient transmission of the radiant energy when the instrument is deployed. An "ablative fluid" in this context is any fluid that can serve as a conductor of the radiant energy. This fluid can be a physiologically compatible fluid, such as saline, or any other non-toxic aqueous fluid that is substantially transparent to the radiation. In one preferred embodiment, the fluid is released via one or more exit ports in the housing and flows between the projection balloon and the surrounding tissue, thereby filling any gaps where the balloon does not contact the tissue. The fluid can also serve an irrigation function by displacing any blood within the path of the radiant energy, which could otherwise interfere because of the highly absorptive nature of blood with respect to radiant light energy.

Similarly, if the radiant energy is acoustic, aqueous coupling fluids can be used to ensure high transmission of the energy to the tissue (and likewise displace blood that might interfere with the radiant acoustic energy transfer).

The ablative fluids of the present invention can also include various other adjuvants, including, for example, photosensitizing agents and/or pharmacological agents.

As noted above, sensing mechanisms are also disclosed to assist the clinician in selecting the location of the lesion and in ensuring a selected location will result in the formation of a continuous (e.g., vein encircling) lesion. In one embodiment, the sensor employs a plurality of light-transmitting fibers, e.g., an endoscope, to determine whether or not a clear transmission pathway has been established (e.g., whether the projection balloon is properly seated and any gaps in contact have been filled by an ablative fluid).

In another aspect of the invention, methods are disclosed for selecting a site for cardiac tissue ablation by positioning a guide wire in a pulmonary vein; and passing a catheter with an endoscope over the guidewire such that it can be disposed in proximity to the vein; and determining whether the catheter is located in a desired location based on an image captured by the endoscope.

More generally, the methods of the present invention can be practiced with or without guidewires. In one embodiment, a guidewire can be used and a catheter with an affixed endoscope can be passed over the guide wire to monitor the placement of a fixed or maneuverable ablation element, thereby permitting a clinician to monitor placement of the catheter and/or ablation element. Alternatively, a guide wire can be used and the catheter passed over the guidewire, followed by the introduction of an endoscope via a lumen or other guide element on or within the catheter, such that the endoscope can confirm the catheter position and/or observe the placement of one or more ablation elements (which can be either fixed to the catheter or independently positionable vis-à-vis a target site).

In yet another method of the invention, the endoscope can be used without a guidewire as a means for monitoring the placement of an ablation device within the heart and/or the positioning of an ablation element, which can be either an integral part of a catheter or independently positionable relative to a catheter.

Most generally, the methods of the present invention encompass the use of endoscopes to determine whether an ablation device is properly located prior to the commencement of an ablation procedure, regardless of the type of ablative element, the type of catheter instrument or the use or non-use of a guidewire. The methods of the present invention further encompass the use of an endoscope to select a desired site, maneuver the instrument to a desired ablation path and monitor ablation as it is carried out.

The inspection methods of the present invention can be used, for example, to determine whether a clear transmission path can be established between an energy emitter and a target tissue site based on imagery captured by the endoscope disposed within the lumen of the catheter. The methods can also be used to determine whether a continuous linear or curvilinear lesion can be formed along a desired path at a target tissue site based on the endoscopic images. Moreover, the methods can be used to also determine whether a continuous circumferential lesion can be formed to surround a target region of the heart, such as one or more pulmonary veins, based on imagery captured by the endoscope disposed within the lumen of the catheter.

The present invention also provides methods for ablating tissue around one or more of the pulmonary veins. One method of ablating tissue comprises positioning a radiant energy emitting element at a distance from a target region of tissue in proximity to the pulmonary vein, providing a blood-free transmission pathway between the emitter and the target region, and then projecting radiant energy to expose the target region and induce a lesion.

In one method according to the invention, a guide wire is first inserted into the femoral vein and advanced through the inferior vena cava, and into the right atrium, and then guided into the left atrium via an atrial septal puncture. The guide wire is advanced until it enters a pulmonary vein. A catheter body is then slid over the guide wire until it is likewise advanced into, or seated proximal to, the pulmonary vein. A projection balloon is then inflated via an inflation fluid to define a transmission pathway to a target tissue site. In addition, a solution can be injected through the instrument to force blood and/or body fluids away from the treatment site.

The guide wire is then removed and replaced with a radiant energy emitter, which is positioned to deliver radiant energy through the projection balloon to induce tissue ablation. The methods of the present invention can further include a position sensing step to assist the clinician in selecting the location of the lesion and in ensuring a selected location will result in the formation of a continuous (e.g., vein encircling) lesion. Either in conjunction with the ablation element, or before deployment of the ablation element, an endoscope is disposed with the instrument to determine whether a clear transmission pathway has been established (e.g., whether the expandable element is properly seated and any gaps in contact have been filled by an ablative fluid).

BRIEF DESCRIPTION OF THE DRAWINGS

The invention will be more fully understood from the following detailed description taken in conjunction with the accompanying drawings, in which like reference numerals designate like parts throughout the figures, and wherein:

FIG. 11 is a schematic cross-sectional illustration of one embodiment of endoscope and ablator assembly according to the invention;

FIG. 12 is an end view, schematic illustration of the endoscope and ablator assembly shown in FIG. 11;

FIG. 15 is a schematic view of a ultrasound heating ablation device employing the contacting sensing apparatus of the present invention; and FIG. 16 is a schematic illustration of a translation system for independently positioning the endoscope and ablation components of an endoscope/ablator assembly during a procedure.

DETAILED DESCRIPTION

Figure 1:
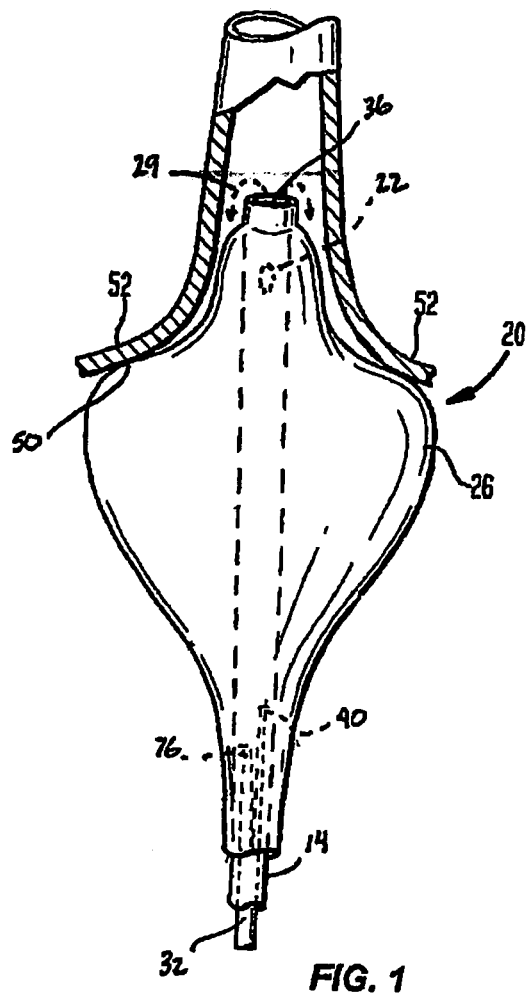
FIG. 1 is a schematic view of an endoscope-guided cardiac ablation instrument according to the invention.

FIG. 1 provides a schematic, cross-sectional view of a coaxial catheter ablation instrument 20 according to the invention, including an elongate body 14 and a projection balloon 26 inflatable via one or more ports 22. The instrument is preferably designed such that upon disposition within the heart (e.g., proximal to a pulmonary vein), the projection balloon can be inflated such that a shoulder portion 50 of the balloon 26 will be urged into close proximity with a target region 52 of cardiac tissue (e.g. an annular region of the atrial heart wall surrounding the ostium of a pulmonary vein).

It should be understood that the embodiments illustrated in the drawings are only a few of the cardiac ablation instruments that can utilized the present invention. Further descriptions of other embodiments can be found, for example, in commonly owned, co-pending U.S. patent application Ser. No. 10/357,156, filed Feb. 3, 2003 and U.S. patent application Ser. No. 09/924,393, filed Aug. 7, 2001, both of which are expressly incorporated by reference.

The instrument can also include one or more ports 36 for delivering ablative fluid to the target region. When the device employs radiant energy ablation, the ablative fluid is preferably an energy transmissive medium, which helps deliver light, radiation or acoustic energy from a radiant energy source to a target tissue region. In the case of electrical resistance or conductive heating (or cryogenic cooling), an ablative fluid is also useful to help conduct electrical current or heat to the target site. The ablative fluid also serves to clear blood from the vicinity of the instrument and compensate for irregularities in the shape of the heart that might otherwise compromise the seating of the instrument. The ablative fluid thus provides a clear transmission pathway external to the balloon.

Within the projection balloon 26 a radiant energy emitter 40 is shown disposed remotely from the target tissue (e.g., within a central lumen of the catheter body 14 or otherwise disposed within the balloon). In one embodiment, the radiant energy source includes at least one optical fiber coupled to a distal light projecting, optical element, which cooperate to project ablative light energy through the instrument to the target site. The catheter body, projection balloon and inflation/ablation fluids are all preferably substantially transparent to the radiant energy at the selected wavelength to provide a low-loss transmission pathway from the ablation element 40 to the target.

Also disposed within the instrument is a reflectance sensor, preferably an endoscope 76 capable of capturing an image of the target site and/or the instrument position. The endoscope is typically an optical fiber bundle with a lens or other optical coupler at its distal end to receive light. The reflectance sensor/endoscope can also include an illumination source, such as an optical fiber coupled to a light source. Suitable endoscopes are available commercially from various sources including, for example, Myriad Fiber Imaging Tech, Inc. of Southbridge, Mass. The endoscope can further include an optical head assembly, as detailed in more detail below, to increase the field of view.

The term "endoscope" as used herein is intended to encompass optical imaging devices, generally, including but not limited to endoscopes, fiberscopes, cardioscopes, angioscopes and other optical fiber-based imaging devices. More generally, "endoscope" encompasses any light-guiding (or waveguide) structure capable of transmitting an "image" of a object to a location for viewing. The viewing location can be direct, e.g., an eyepiece, or indirect, e.g., an image capture device, such as a CCD camera, which converts image data into a video display.

Figure 1A:
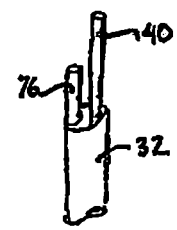
FIG. 1A is a schematic view of an endoscope/ablation element assembly according to the invention.

FIG. 1A is a schematic view of an endoscope/ablation element assembly 32 according to the invention including an ablation element 40 and an endoscope 76. The assembly 32 can be adapted for axial movement within an inner lumen of catheter body 14. In one preferable embodiment, ablation element 40 and endoscope 76 are adapted for independent axial movement within the assembly 32.

Figure 2:
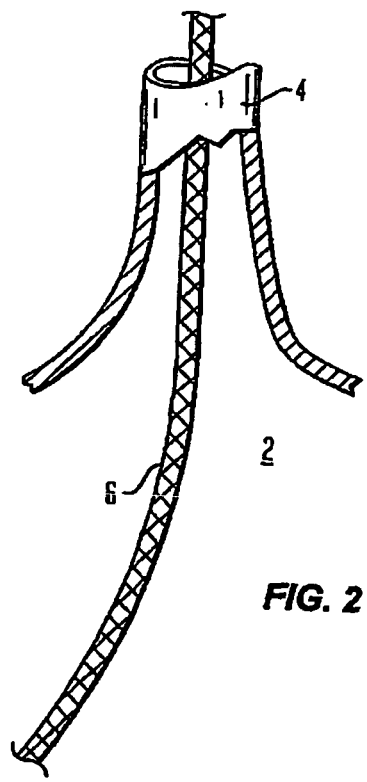
FIG. 2 is a schematic illustration of an initial step in performing ablative surgery according to the invention, in which a guide wire is introduced into a heart and passed into a pulmonary vein.

FIG. 2 is a schematic illustration of an initial step in performing ablative surgery with radiant energy according to the invention, in which a guide wire 6 is introduced into a heart 2 and passed into a pulmonary vein 4.

Figures 3A, 3B:
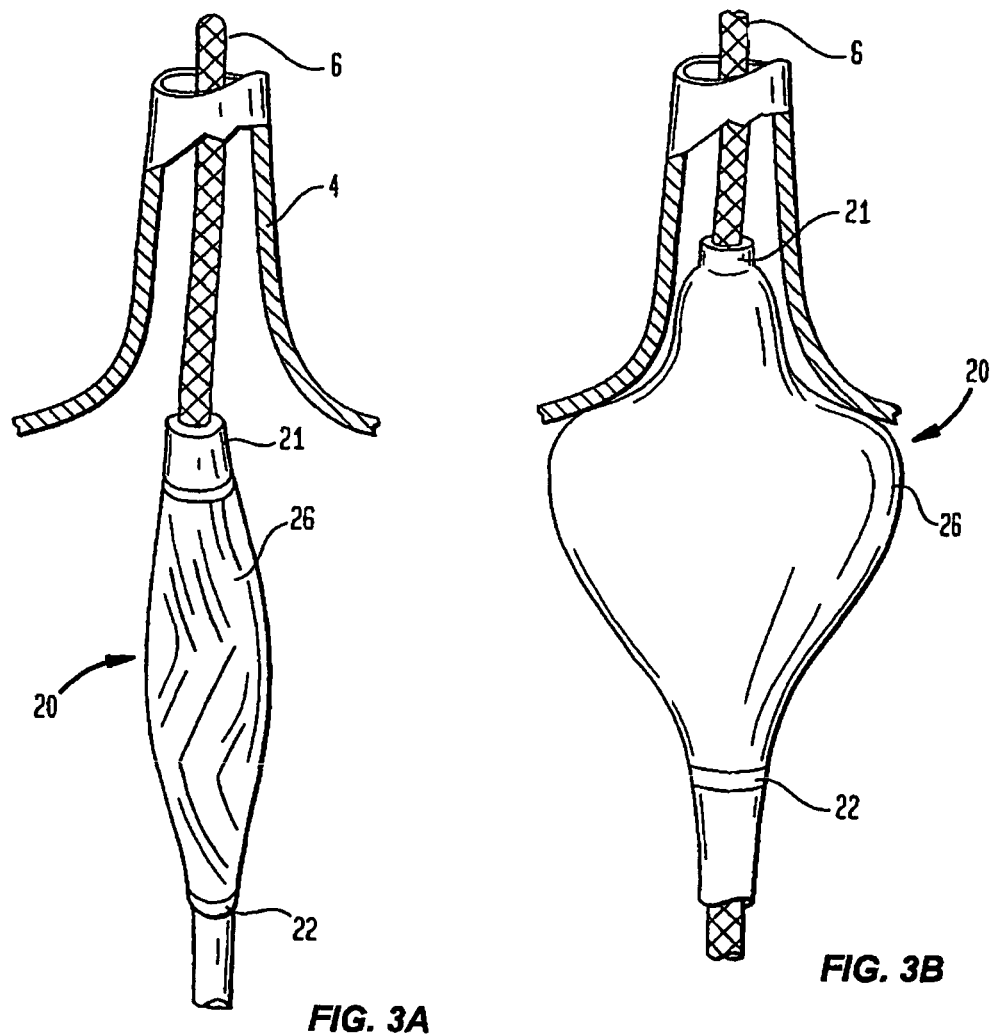
FIG. 3A is a schematic illustration of a further step in performing ablative surgery according to the invention, in which a catheter carrying a projection balloon structure is slid over a guide wire.
FIG. 3B is a schematic illustration of a further step in performing ablative surgery with the embodiment illustrated in FIG. 3A, in which the projection balloon element is inflated to define a projection pathway for radiant energy ablation of cardiac tissue.

FIG. 3A is a schematic illustration of a method of performing ablative surgery with radiant energy according to the invention. After guide wire 6 is be introduced into a heart and passed into a pulmonary vein 4, catheter 20, carrying projection balloon structure 26, is slid over the guide wire 6. This catheter 20 can further include at least one internal fluid passageway (not shown) for inflation of the balloon 26, which is sealed to the body of the catheter 20 by distal seal 21 and proximal seal 22, such that the introduction of an inflation fluid into the balloon 26 can inflate the balloon.

FIG. 3B illustrates how the projection balloon 26 can then be inflated to define a projection pathway for radiant energy ablation of cardiac tissue. The expanded projection balloon defines a staging through which radiant energy can be projected in accordance with the invention. In one preferred embodiment, the projection balloon is filled with a radiation-transmissive fluid so that radiant energy from an energy emitter can be efficiently passed through the instrument to a target region of cardiac tissue.

The projection balloons described herein can be preshaped to form parabolic like or various other shapes (e.g., to assist in seating the instrument at the mouth of a pulmonary vein or otherwise engaging the vein ostium or other anatomically defined regions of the heart). This can be accomplished, for example, by shaping and melting a TEFLON® film in a preshaped mold to effect the desired form. The projection balloons of the present invention can be made, for example, of thin wall polyethylene teraphthalate (PET) with a thickness of the membranes of about 5-50 micrometers.

It should be noted that it is not necessary for the projection balloon 26 to contact the target tissue in order to ensure radiant energy transmission. One purpose of the projection balloon is simply to clear a volume of blood away from the path of the energy emitter. With reference again to FIG. 1, an ablative fluid 29 can be employed outside of the instrument (e.g., between the balloon 26 and the target region 52) to ensure efficient transmission of the radiant energy when the instrument is deployed. The ablative fluid in this context is any fluid that can serve as a conductor of the radiant energy. This ablative fluid can be a physiologically compatible fluid, such as saline, or any other non-toxic aqueous fluid that is substantially transparent to the radiation. As shown in FIG. 1, the fluid 29 can be released via one or more exit ports 36 in the first catheter body 14 to flow between the projection balloon 26 and the surrounding tissue, thereby filling any gaps where the balloon 26 does not contact the tissue. The fluid 29 can also serve an irrigation function by displacing any blood within the path of the radiant energy, which could otherwise interfere with the radiant light energy transmission to the target region 52.

For alternative designs for delivery of ablative and/or irrigation fluids, see commonly-owned, U.S. patent application Ser. No. 09/660,601, filed Sep. 13, 2000 entitled "Balloon Catheter with Irrigation Sheath," the disclosures of which are hereby incorporated by reference. For example, in one embodiment described in patent application Ser. No. 09/660,601, the projection balloon can be partially surrounded by a sheath that contains pores for releasing fluid near or at the target ablation site. One of ordinary skill in the art will readily appreciate that such pores can vary in shape and/or size. A person having ordinary skill in the art will readily appreciate that the size, quantity, and placement of the fluid ports of various designs can be varied to provide a desired amount of fluid to the treatment site.

Figure 4:
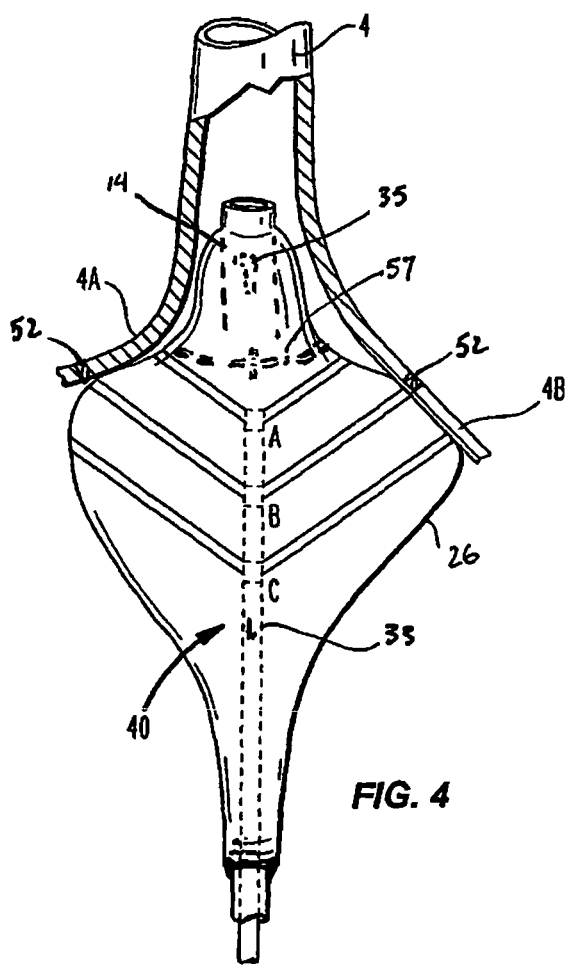
FIG. 4 is a schematic illustration of a further step in performing ablative surgery with the embodiment illustrated in FIGS. 3A-3B, in which the guide wire is removed and replaced by a radiant energy emitter located remote from the lesion site but in a position that permits projection of radiant energy onto a target region of the heart in which an asymmetric vein mouth is encountered and further showing how the position of the radiant energy emitter can be adjusted to select a desired location.

FIG. 4 is a schematic illustration of a further step in performing ablative surgery according to the invention, in which the guide wire is removed and replaced by a energy emitter 40 located remote from the desired lesion site 52 but in a position that permits projection of radiant energy onto a target region of the heart. The energy emitter can be introduced into the instrument via the lumen of the inner catheter. In the illustrated embodiment, shown in more detail in FIG. 7, the energy emitter 40 is a radiant energy emitter and includes at least one optical fiber 42 coupled to a distal light projecting, optical element 43, which cooperate to project ablative light energy through the instrument to the target site. In one embodiment, optical element is a lens element capable of projecting an annular (ring-shaped) beam of radiation, as described in more detail in commonly owned U.S. Pat. No. 6,423,055 issued Jul. 22, 2002, herein incorporated by reference. In another embodiment, the optical element is adapted to project an arc-like pattern of radiation and the energy emitter can be rotated and/or translated to encircle the pulmonary vein. Alternatively, the radiant energy emitter can be an ultrasound or microwave energy source, as described in more detail below (in connection with FIGS. 9-10).

Figure 5:
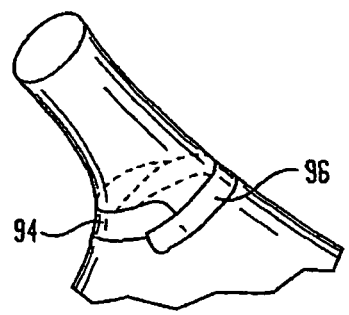
FIG. 5 illustrates how a continuous, vein-encircling lesion can be formed by two partially-encircling lesions.

FIGS. 4 and 5, taken together, also illustrate an advantageous feature of the present invention, namely, the ability to select the location a lesion independent of the instrument design. Because the radiant energy emitter does not require contact with a target tissue region and is, in fact, decoupled from the rest of the instrument, the present invention permits the clinician to select a desired target region by simply moving the emitter (e.g., within the lumen of the catheter). As shown in FIG. 4, the radiant energy emitter can be positioned to form a wide circumferential lesion (when the shape of the pulmonary vein ostium warrants such a lesion) by positioning the radiant energy emitter at the rear of the projection balloon—at a distance from the target tissue denoted as "C". Alternatively, a smaller diameter lesion can be formed by positioning the radiant energy emitter closer to the front of the project balloon, as shown in positions "A" or "B". Smaller lesions can be preferably when the geometer of the vein ostium presents a sharper change in diameter, as shown by schematic wall segment 4B. It should be appreciated that it may be desirable to change the intensity of the emitted radiation depending upon the distance it must be projected; thus a more intense radiant energy beam may be desirable in the scheme illustrated in position "C" in comparison with position "A.". The energy emitter 40 and catheter body 14 can each include one or more markers (shown schematically as elements 33 and 35 respectively) to aid in determining the location or tracking movements of the elements. Markers 33 and 35, for example, can be radioopaque lines that can visualized fluoroscopically.

In addition the expandable element can include an orientation marker 57 which can be visualized endoscopically to visualize the position and/or orientations of the instrument. Each of the markers 33, 35 and 57 can be suitably shaped to provide three-dimensional information. For example, the markers can be shaped in the form of a "T" or an "L" (or, in the case of the circular, balloon neck marker 57, with one or more azimuthal cross-marks) to assist in orientation. Various other marker mechanisms, such as magnetic, capacitive or optical markers, can also be used.

Typically with prior art devices, the target site, e.g., the ostium of a pulmonary vein, can only be located by fluoroscopic inspection during injection of a contrast medium into the vein. Such images are transient. Location of the ablation catheter itself, even with radioopaque markers is likewise difficult because of the geometry of the heart. Moreover the heart's structure is largely invisible during fluoroscopic inspection.

The endoscopic guidance systems of the present invention coupled with the use of orientation markers can help overcome these problems. The use of radioopaque markers on the endoscope and/or the catheter allow the user to orient the ablation instrument relative to the pulmonary vein and permit anatomical features seen via the endoscope to be combined with fluoroscopic information. Orientation markers, such as elements 33 and 35 can be used to determine the angular position of the instrument relative to structures such the ostia and also provide a measure of how far a movable element, such as the energy emitter 40, has been advanced within the instrument. (It should be appreciated that numerous other marker schemes can be employed to achieve these objectives, including ring markers on either the energy emitter and/or the catheter body.)

Similarly, the ring marker shown as element 57 on the projection balloon 26 can be replaced by a series of rings. Alternatively, if the endoscope is maintained in a fixed position relative to the balloon, physical markers can be replaced with virtual markers generated electronically as part of the display. Such information is particularly useful in selection one or more of alternative sites for ablation. In addition to the movable energy emitters described herein, the invention can be used in conjunction with two or more fixed ablation elements (e.g., resistive heating bands of different circumferences) to select the most appropriate one (or set) of the ablation elements to be activated for lesion formation.

The endoscopic guidance systems of the present invention can further be used to position any movable point source of ablative energy, e.g., a rotating contact or radiant ablation element in lieu of a slidably positionable source or together therewith, such that the desired path for circumferential can be visualized and followed by the ablation element. Most generally, the endoscopic guidance systems of the invention can be used together with various fluoroscopic or other imaging techniques to locate and position any one of the various instruments necessary for cardiac ablation.

The ability to position the energy emitter, especially when radiant light is employed as the ablation modality, also permits endoscopic aiming of the energy. For example, an aiming light beam can be transmitted via the catheter to the target site such that the physician can visualize where the energy will be delivered. Thus, endoscopic guidance permits the user to see where energy will be projected at various locations of the energy emitter. Thus, if the instrument is designed to project light in an annular ring around the ostium of a pulmonary vein, the aiming beam can be projected down the same optical delivery path as would the radiant energy. If the "aiming ring" is projected onto a region of the atrium where a clear transmission pathway is seen (e.g., there is continuous contact (or the desired lesion path is otherwise cleared of blood), then the physician can begin the procedure. If, on the other hand, a clear transmission pathway is not seen at a particular location of the ablation element, then the ablation element can be moved until a clear lesion pathway is found.

Although this "aiming" feature of the invention has been described in connection with radiant light energy sources, it should be clear that "aiming" can be used advantageously with any radiant energy source and, in fact, it can also assist in the placement of fixed or contact-based ablation elements. Most generally, endoscope-guidance can be combined with an aiming beam in any cardiac ablation system to improve positioning and predetermination of successful lesion formation.

The terms "visual," "visualize" and derivatives thereof are used herein to describe both human and machine uses of reflectance data. Such data can take the form of images visible to a clinician's eye or any machine display of reflected light, e.g., in black & white, color or so-called "false color" or color enhanced views. Detection and display of reflected energy measurements outside the visible spectrum are also encompassed. In automated systems such visual data need not be displayed but rather employed direct by a controller to aid in the ablation procedure.

FIG. 4-5 further illustrates the unique utility of the multi-positionable, radiant energy ablation devices of the present invention in treating the complex cardiac geometries that are often encountered. As shown in the figure, the mouths of pulmonary veins typically do not present simple, funnel-shaped, or regular conical surfaces. Instead, one side of the ostium 4B can present a gentle sloping surface, while another side 4A presents a sharper bend. With prior art, contact-heating, ablation devices, such geometries will result in incomplete lesions if the heating element (typically a resisting heating band on the surface of an expandable element) can not fully engage the tissue of the vein or ostium. Because the position of the heating band of the prior art devices is fixed, when it does not fully contact the target tissue, the result is an arc, or incompletely formed ring-type, lesion that typically will be insufficient to block conduction.

FIG. 4 illustrates how the slidably positionable energy emitters of the present invention can be used to avoid this problem. Three potential positions of the emitter 40 are shown in the figure (labeled as "A", "B" and "C"). As shown, positions A and C may not result in optimal lesions because of gaps between the balloon and the target tissue. Position B, on the other hand, is preferable because circumferential contact has been achieved. Thus, the independent positioning of the energy source relative to the balloon allows the clinician to "dial" an appropriately ring size to meet the encountered geometry. (Although three discrete locations are shown in FIG. 4, it should be clear that emitter can be positioned in many more positions and that the location can be varied in either discrete intervals or continuously, if so desired.)

Moreover, in some instances the geometries of the pulmonary vein (or the orientation of the projection balloon relative to the ostium) may be such that no single annular lesion can form a continuous conduction block. Again, the present invention provides a mechanism for addressing this problem by adjustment of the location of the energy emitter to form two or more partially circumferential lesions. As shown in FIG. 5, the devices of the present invention can form a first lesion 94 and a second lesion 96, each in the form of an arc or partial ring. Because each lesion has a thickness (dependent largely by the amount of energy deposited into the tissue) the two lesions can axially combine, as shown, to form a continuous encircling or circumscribing lesion that blocks conduction.

Figure 6:
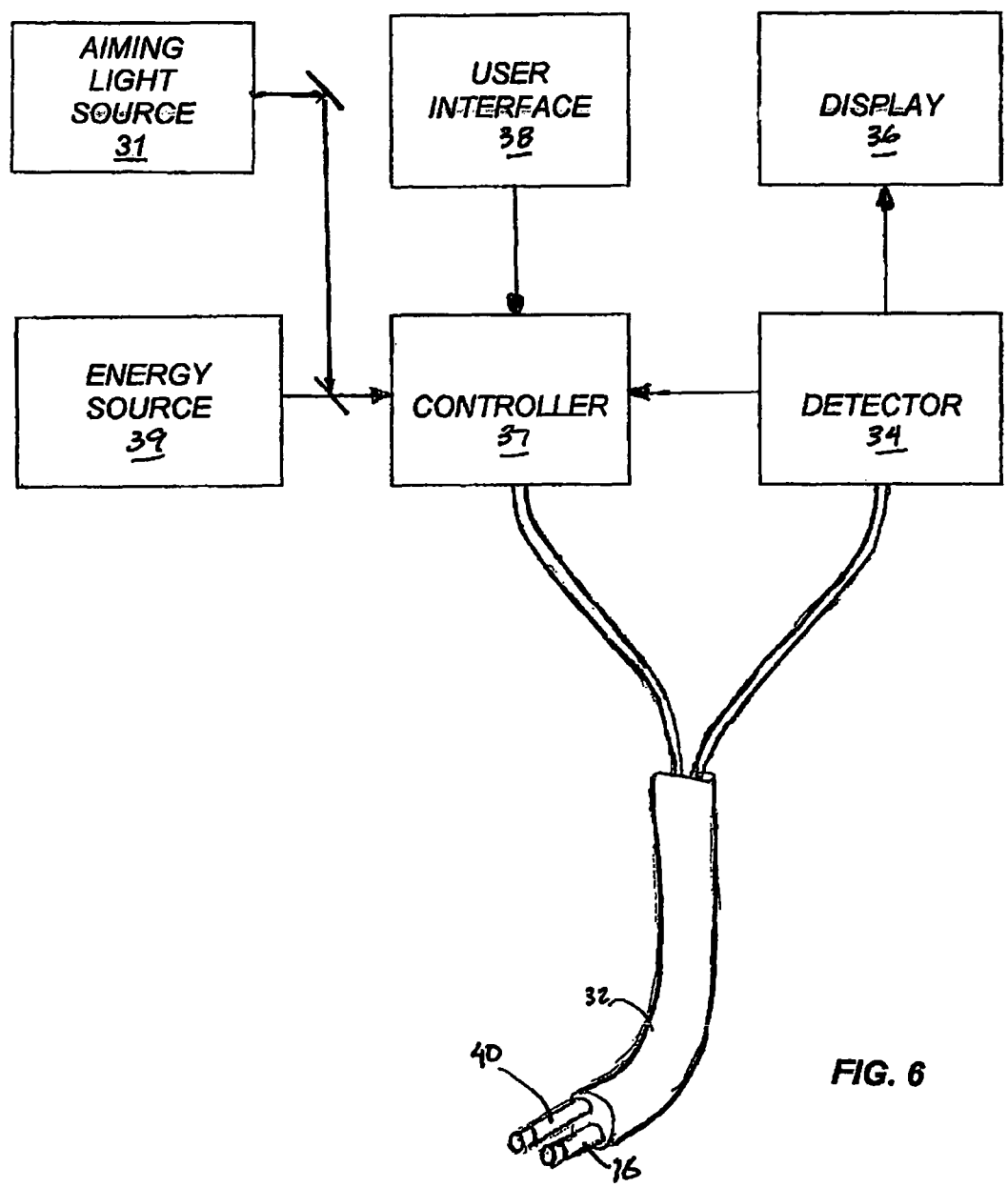
FIG. 6 is a schematic block diagram of the components of an endoscope-guided cardiac ablation system according to the invention.

FIG. 6 is a schematic block diagram shown the endoscope/ablator assembly 32 comprising endoscope 76 and ablation element 40 connected to an analyzer system. The analyzer system further includes a detector 34 for detecting reflected light (and preferable for generating a image). The output of the detector 34 can be transmitted to a display 36 for clinician viewing. The display 36 can be a simple eyepiece, a monitor or a heads-up projection onto glasses worn by members of the surgical team. The system can further include an energy source 39, a controller 37 and a user interface 38. In use, the endoscope 76 captures images which can be processed by the detector 34 and/or controller 37 to determine whether a suitable ablation path can be created. An aiming light source 31 can also be used visualize the location where energy will be delivery to the tissue. If a suitable ablation path is seen by the surgeon, the controller 37 can transmit radiant energy from the ablation element 40 to a target tissue site to effect ablation. The controller can further provide simulated displays to the user, superimposing, for example, a predicted lesion pattern on the image acquired by the detector or superimposing dosimetry information based on the lesion location. The controller can further include a memory for storing and displaying data, such as pre-procedure images, lesion predictions and/or actual outcomes. The controller can further provide a safety shutoff to the system in the event that a clear transmission pathway between the radiant energy source and the target tissue is lost during energy delivery.

Figure 7:
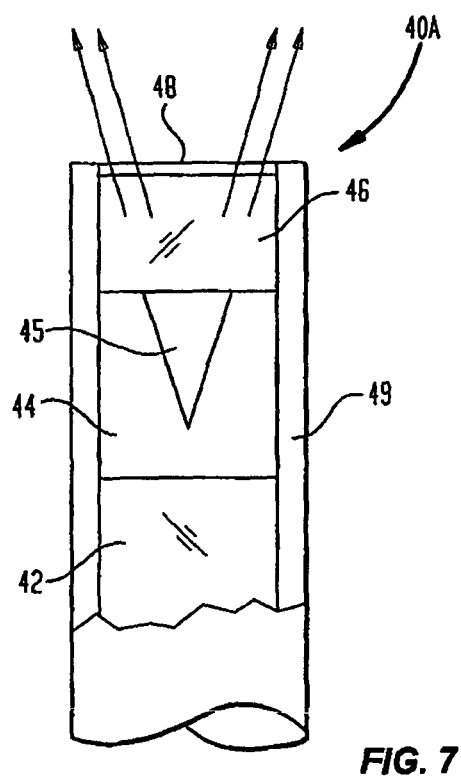
FIG. 7 is a schematic illustration of one embodiment of a radiant light energy emitter according to the invention.

FIG. 7 is a schematic illustration of one embodiment of a radiant energy emitter 40A according to the invention. In one preferred embodiment, the radiant energy is electromagnetic radiation, e.g., coherent or laser light, and the energy emitter 40A projects an hollow cone of radiation that forms an annular exposure pattern upon impingement with a target surface. For example, radiant energy emitter 40A can include an optical fiber 42 in communication with an annulus-forming optical waveguide 44 having a concave interior boundary or surface 45. The waveguide 44 passes an annular beam of light to a graded intensity (GRIN) lens 46, which serves to collimate the beam, keeping the beam width the same, over the projected distance. The beam that exits from the distal window 48 of energy emitter 40 will expand (in diameter) over distance, but the energy will remain largely confined to a narrow annular band. Generally, the angle of projection from the central axis of the optical fiber 42 or waveguide 44 will be between about 20 and 60 degrees (for a total subtended angle of about 40 to about 120 degrees).

The diameter of the annular beam of light will be dependent upon the distance from the point of projection to point of capture by a surface, e.g., a tissue site, e.g., an interstitial cavity or lumen. Typically, when the purpose of the radiant energy projection is to form a transmural cardiac lesion, e.g., around a pulmonary vein, the diameter of the annular beam will be between about 10 mm and about 33 mm, preferably greater than 10 mm, greater than 15 mm, greater than 20 mm, and most preferably, greater than or equal to 23 mm. Typically, angle of projected annular light is between about 20 and about 60 degrees, preferably between about 45 and about 55 degrees, most preferably in some applications about 50 degrees (total subtended angle 100 degrees).

Preferred energy sources for use with the percutaneous ablation instruments of the present invention include laser light in the range between about 200 nanometers and 2.5 micrometers. In particular, wavelengths that correspond to, or are near, water absorption peaks are often preferred. Such wavelengths include those between about 805 nm and about 1060 nm, preferably between about 900 nm and 1000 nm, most preferably, between about 915 nm and 980 nm. In a preferred embodiment, wavelengths around 915 nm or around 980 nm are used during endocardial procedures. Suitable lasers include excimer lasers, gas lasers, solid state lasers and laser diodes. One preferred AlGaAs diode array, manufactured by Spectra Physics, Tucson, Ariz., produces a wavelength of 980 nm.

The optical waveguides, as described in above, can be made from materials known in the art such as quartz, fused silica or polymers such as acrylics. Suitable examples of acrylics include acrylates, polyacrylic acid (PAA) and methacrylates, polymethacrylic acid (PMA). Representative examples of polyacrylic esters include polymethylacrylate (PMA), polyethylacrylate and polypropylacrylate. Representative examples of polymethacrylic esters include polymethylmethacrylate (PMMA), polyethylmethacrylate and polypropylmethacrylate. In one preferred embodiment, the waveguide 44 is formed of quartz and fused to the end face of fiber 42.

Internal shaping of the waveguide can be accomplished by removing a portion of material from a unitary body, e.g., a cylinder or rod. Methods known in the art can be utilized to modify the waveguide to have tapered inner walls, e.g., by grinding, milling, ablating, etc. In one approach, a hollow polymeric cylinder, e.g., a tube, is heated so that the proximal end collapses and fuses together, forming an integral proximal portion which tapers to the distal end of the waveguide. In another approach, the conical surface 45 can be formed in a solid quartz cylinder or rod by drilling with a tapered bore.

Waveguide 44 can be optical coupled to optical fiber 42 by various methods known in the art. These methods include for example, gluing, or fusing with a torch or carbon dioxide laser. In one embodiment, waveguide 44, optical fiber 42 and, optionally, a gradient index lens (GRIN) 46 are in communication and are held in position by heat shrinking a polymeric jacket material 49, such as polyethylene terephthalate (PET) about the optical apparatus 40.

Figure 8:
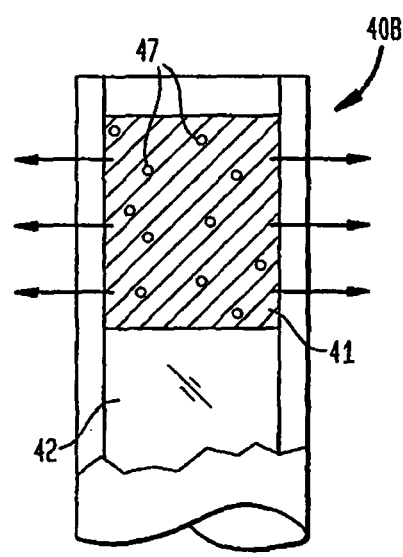
FIG. 8 is a schematic illustration of another embodiment of a radiant light energy emitter according to the invention.

FIG. 8 is a schematic illustration of another embodiment of a radiant energy emitter 40B according to the invention in which optical fiber 42 is coupled to a light diffuser 41 having light scattering particles 47 to produce a sidewise cylindrical exposure pattern of ablative radiation. This embodiment can be useful, for example, in creating a lesion within a pulmonary vein. With reference again to FIG. 4, it should be clear that the radiant energy emitter of the design shown in FIG. 14 can be advanced to the front of the projection balloon to permit diffuse exposure of a pulmonary vein ostium if a lesion is desired in that location. For further details on the construction of light diffusing elements, see U.S. Pat. No. 5,908,415 issued to Sinofsky on Jun. 1, 1999, herein incorporated by reference.

Figure 9:
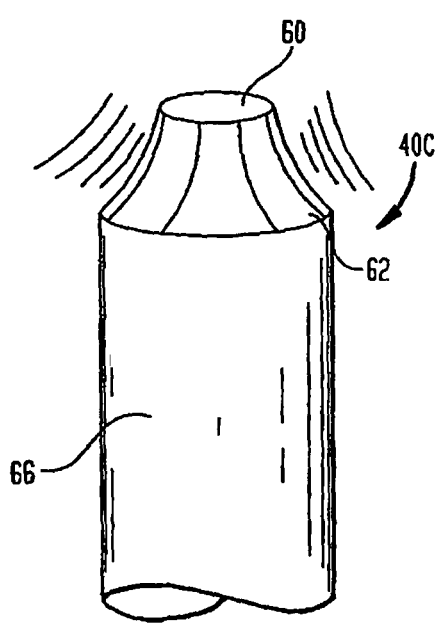
FIG. 9 is a schematic illustration of an alternative embodiment of a radiant energy emitter according to the invention employing ultrasound energy.

FIG. 9 illustrates an alternative embodiment of a radiant energy emitter 40C in which an ultrasound transducer 60, comprising individual shaped transducer elements (and/or lenses or reflectors) 62 which direct (project) the ultrasound energy into a cone of energy that can likewise form an annular exposure pattern upon impingement with a target surface. The emitter 40C is supported by a sheath 66 or similar elongate body, enclosing electrical leads, and thereby permitting the clinician to advance the emitter through an inner lumen of the instrument to a desired position for ultrasound emission.

Figure 10:
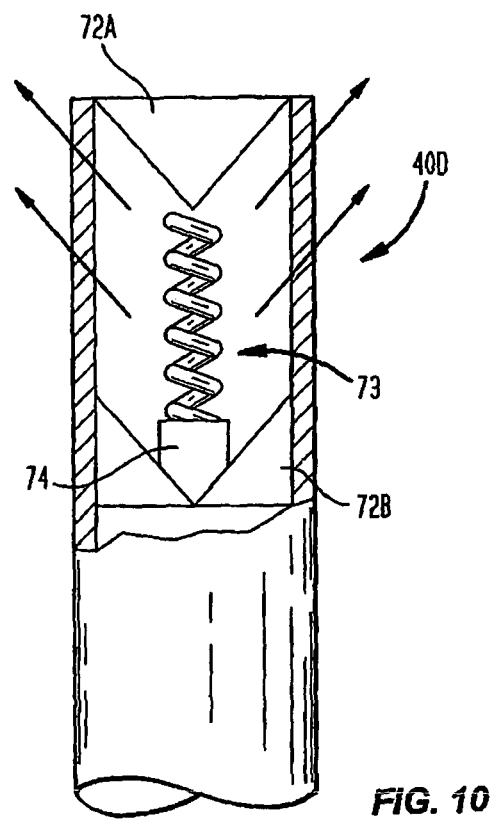
FIG. 10 is a schematic illustration of an alternative embodiment of a radiant light energy emitter according to the invention employing microwave or ionizing radiation.

Yet another embodiment of a radiant energy emitter 40D is illustrated in FIG. 10 where microwave energy is similarly focused into an annular exposure beam. As shown in FIG. 10, the radiant energy emitter can include a coaxial transmission line 74 (or similar electrical signal leads) and a helical coil antenna 73. Radiation reflectors 72A and 72B cooperated to shield and direct the radiation into a cone. In other embodiments, a radioisotope or other source of ionizing radiation can be used in lieu of the microwave antenna 73, again with appropriate radiation shielding elements 72A and 72B to project a beam of ionizing radiation.

FIGS. 11 and 12 illustrate one embodiment of a contact sensor according to the invention incorporated into a radiant emitter assembly. The assembly can includes an assembly body 32 that encases an endoscope/ablator assembly and facilitates slidable positioning within an inner lumen of catheter body 14. The assembly further includes an energy emitter 40 (e.g., like those described above in connection with FIGS. 7-10) which can also act as the sensing fiber. In the illustrated embodiment, an ablation element 40 is shown which can act as an illumination light source (when operated a low power). If the ablative element of the invention is properly positioned within the heart, light transmitted via such ablation element will strike the target region, be reflected back, and detected by the reflectance sensor 76. It should be clear that the invention can be practiced with various numbers of illuminating and/or sensing elements, and with or without use of the energy emitter as an element in the contact sensing module. The emitter and the endoscope can each move independently, if desired. Moreover, ultrasound emitters and detectors can also be used in the same manner in lieu of the light reflecting mechanisms to determine contact. In any event, the output signals of the sensors can be electronically processed and incorporated into a display.

The devices of the present invention can further include illumination elements that are capable of diffusing light to a large contact area of tissue by employing a scattering medium at the distal end of the illumination fiber. Examples of this diffusing material can be a matrix of titanium dioxide particles suspended in cured silicone. This diffusing medium allows high intensity light to be uniformly diffused over a large area preferably over an area greater than 40 mm in diameter.

Endoscope 76, as shown in FIG. 11, can include an optical fiber bundle 78 for transmitting the captured image back to a detector and display, as well as a lenses 136 and 140 which provide an enhanced field of view. Such field enhancing elements preferably increase the field of view to greater than 50 degrees, more preferably to about 70 degrees or higher. Typically, commercially available endoscopes have a field of view of about 50 degrees or less in air. However, when immersed in water or similar fluids, the field of view of the endoscope is further reduced due to the refractive index difference between water and air. As explained in more detail below, a greater field of view is very important to endoscopic guidance.

The endoscopes of FIGS. 11-12 provide the ability to position the percutaneous ablation instruments of the present invention at a treatment site such that proper location of the energy emitter vis-à-vis the target tissue (as well a satisfactory degree of contact between the projection balloon and the tissue) is achieved.

Figure 11A:
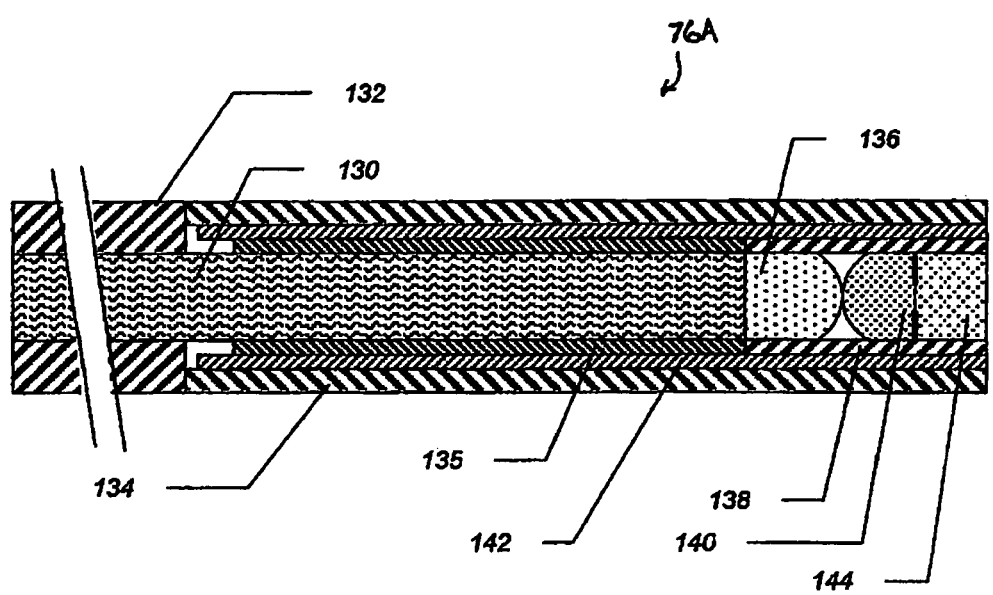
FIG. 11A is a more detailed schematic cross-sectional view of an endoscope according to the invention.

FIG. 11A provides a detailed schematic illustration of an endoscope 76A with enhanced field of view. The endoscope can include a fiber bundle 130 within a protective polyimide tube 132 coupled to distal stainless steel tube 134 in which the field-enhancing optics are disposed. Within distal tube 134, an imaging lens 136 and an objective lens 140 are situated, together with a centering and connecting tubes (e.g., tube 135 and 142) as may be needed to secure the lenses in place. (It should be appreciated that various lens combination or compound lens structures can be substituted for the elements shown in FIG. 11A.)

The endoscope 76A is designed to have a wide field of view even while it is immersed in liquid. The liquid in which it is immersed typically can be either physiological saline in the inner lumen of the catheter or deuterium oxide which is one preferred medium for filling applicants' projection balloon. Both of these liquids have essentially the same index of refraction. To achieve the wide field of view a lens system shown FIG. 11A can be used. The lens system consists of two plano-convex lenses 136 and 140 arranged as shown along with an apertured window 144. High index of refraction materials are preferably used for the lenses. Suitable materials include sapphire, cubic zirconia or high index glass materials. Alternatively, air-filled optical structures can be substituted for the solid lenses shown in the figure. All these materials are readily available as small diameter spheres with optical quality surfaces. The spheres can be made into hemispheres and the diameter of the hemispheres are reduced using common lens grinding technology. The aperture can be constructed by metallizing one surface of flat glass plate. The central aperture hole is created by masking the flat glass before the metallization or removing the metallization with a laser.

Sample specifications for the lens elements are as follows:

TABLE 1

| Lens Specifications | | | | |
|---|---|---|---|---|
| Element Name | Material | Spherical Radius | Overall Diameter | Center thickness |
| Object Lens | Cubic Zirconia or high index glass | 0.200 mm | 0.400 mm | 0.244 mm |
| Image Lens | Saphire or high index glass | 0.300 mm | 0.400 mm | 0.187 mm |
| Aperture Window 0.060 mm dia. | Schott B270 Grade A glass | Flat on both Faces | 0.400 mm | 0.125 mm |

This lens system has field of view of slightly larger than 110° when immersed in water, an f number of about 2.5 and a depth of field that provides acceptable focus over a range of object distances from 13 mm to 40 mm. Acceptable focus is that degree of focus that results in minimum resolvable spot diameters that are close in size to 5 microns, which is the size of the individual fibers in the image bundle of the endoscope.

In the design described above the lens elements can be assembled so the spherical surfaces touch and therefore the elements are self-locating when assembled in a small lens cell tube 138 with an inner diameter just slightly larger than the outer diameter of the lens elements. Once the lens cell is fabricated it is attached to the image bundle using techniques common to those skilled in the art. The general assembly can use precise diameter tubes of polyimide whose dimensions can be controlled very precisely and whose wall thicknesses can be made very thin.

The ability have a field of view greater that 50 degrees (and, preferably, in some applications, greater than 70 degrees, or 90 degrees) can be important because of the geometry of the heart and the ablation elements. Visualization the ostium of a pulmonary vein inherently requires a wide field of view. Moreover, the ablation element (including any expandable element) must be short because of the limited space available within the atrial chamber. These two factors combine to require the placement of the endoscope close to the vein and an even wider field of view is desirable, typically greater than 70 degrees, in order to visualize the target region and the instrument's position relative to the target region. Moreover, the wide field of view allows the clinician to see well proximal to the apex of the balloon; thus providing the ability to determine if the instrument is placed too distally in the pulmonary vein.

The endoscopes of the present invention can also be used in conjunction with other optical reflectance measurements of light scattered or absorbed by blood, body fluids and tissue. For example, white light projected by an illumination source toward tissue has several components including red and green light. Red light has a wavelength range of about 600 to about 700 nanometers (nm) and green light has a wavelength range of about 500 to about 600 nm. When the projected light encounters blood or body fluids, most if not all green light is absorbed and hence very little green or blue light will be reflected back toward the optical assembly which includes a reflected light collector. As the apparatus is positioned such that blood and body fluids are removed from the treatment field cleared by an inflated balloon member, the reflectance of green and blue light increases as biological tissue tends to reflect more green light. As a consequence, the amount of reflected green or blue light determines whether there is blood between the apparatus and the tissue or not.

Thus, the endoscopic displays of the present invention can incorporate filters (or generate "false-color" images) that emphasize the presence or absence of blood in the field. For example, when the inflated balloon member contacts the heart tissue (or is close enough that the balloon and ablative fluid released by the instrument form a clear transmission pathway), more green light will be reflected back into the optical assembly and the collector. The ratio of two or more different wavelengths can be used to enhance the image. Accordingly, a color-enhanced endoscope permit visualization of the instrument and/or the target site, as well as a determination of whether blood precludes the formation of a continuous lesion, e.g., circumferential lesion around the ostium of a pulmonary vein.

Alternatively, spectrographic measurements can be taken in tandem with endoscopic imaging, Thus, reflected light can be transmitted back through a collector, such as an optical fiber to a spectrophotometer. The spectrophotometer (Ocean Optics Spectrometer, Dunedin, Fla., model S-2000) produces a spectrum for each reflected pulse of reflected light. Commercially available software (LabView Software, Austin, Tex.) can isolate values for specific colors and perform ratio analyses.

Once the operator is satisfied with the positioning of the instrument, radiant energy can then be projected to the target tissue region. If the radiant energy is electromagnetic radiation, e.g., laser radiation, it can be emitted onto the tissue site via a separate optical fiber or, alternatively, through the same optical fiber used to transmitting the white, green or red light. The laser light can be pulsed intermittently in synchronous fashion with the positioning/reflecting light to ensure that the pathway remains clear throughout the procedure.

Figure 13:
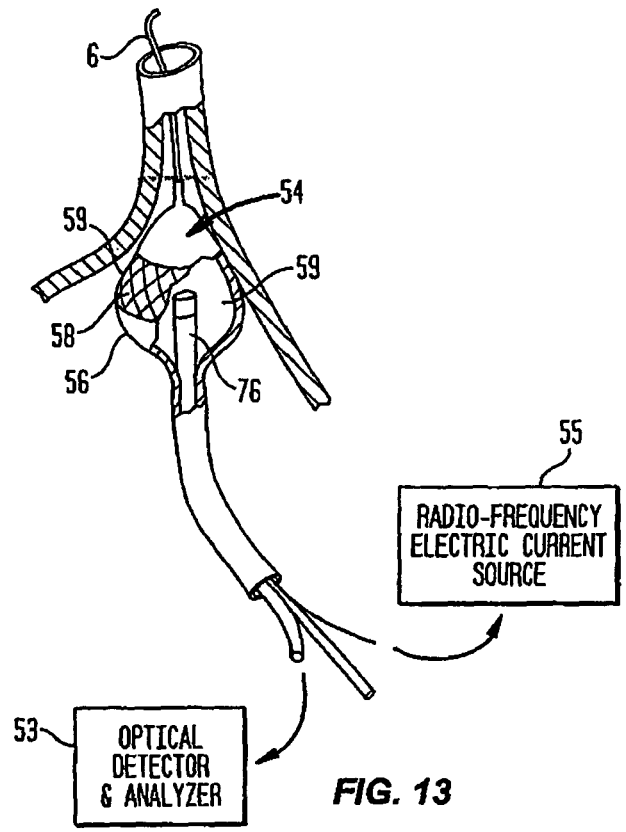
FIG. 13 is a schematic view of a contact heating ablation device employing the endoscope-guiding apparatus of the present invention.

It should be clear that the imaging and contact sensing aspects of the present invention are not limited to radiant energy ablation devices but can also be useful in placement of contact heating or cooling ablation instruments as well. For example, in FIG. 13, a contact-heating device 54 having an expandable element 56 and a contact heating element 58 is shown disposed in a pulmonary vein. The contact heating element can be a line or grid of electrically conductive material printed on the surface of the expandable element. In one embodiment, the expandable element can be substantially opaque to certain wavelengths (e.g., visible light) except for a transparent band 59, on which the contact heating element is situated. The heating wires should also be sufficiently transparent (or cover a substantially small area of the band) so as to not interfere with reflection signal collection. The device 54 can further include a sensor, e.g., an endoscope, disposed within a central lumen of the device having an illuminating fiber and a plurality of collecting fibers.

Figure 14:
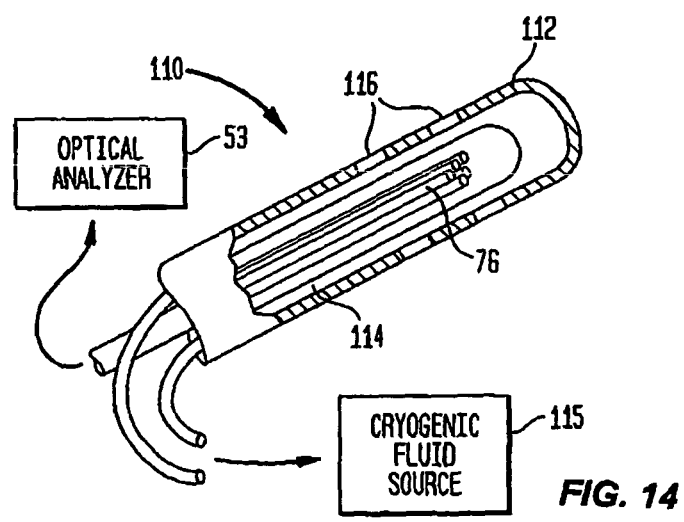
FIG. 14 is a schematic view of a cryogenic ablation device employing the endoscope-guiding apparatus of the present invention.

In FIG. 14, another embodiment of a reflectance sensing or endoscope-guided catheter is shown in the form of a cryogenic ablation catheter 110 having a catheter body 112 and internal conduits 114 for circulation of a cryogenic fluid from a cryogenic fluid source 115. The catheter body can include an expandable portion, e.g., a balloon structure, and further includes conductive regions 116 where the cold temperature can be applied to tissue. The endoscope 76 of the present invention can be disposed in proximity to the conductive regions, as shown and used to determine whether tissue contact has been made.

In FIG. 15 yet another application for the contact sensors is shown in connection with an ultrasound, contact-heating balloon catheter 120, having a balloon 122 (similar to that discussed above in connection with FIG. 13) for contacting a pulmonary vein ostium and having an optional band 123 for applying heat to tissue. The ultrasound ablation instrument 120 further includes transducers 124 driven by actuator 125 to heat a desired region of tissue. The instrument 120 can also included reflectors 126 to project the ultrasound energy through the balloon into an annular focus in the target tissue (or at the surface of the balloon). Again, the reflectance or endoscopic sensors 76 of the present invention can be disposed within the balloon or catheter body, as shown, and used to determine whether tissue contact has been made.

In FIG. 16, a translatory mechanism 80 is shown for controlled movement of a radiant energy emitter within the instruments of the present invention. The exemplary positioner 80 is incorporated into a handle 84 in the proximal region of the instrument, where the elongate body 82 of the radiant energy emitter 40 engages a thumb wheel 86 to control advancement and retraction of the emitter. It should be clear that various alternative mechanisms of manual or automated nature can be substituted for the illustrated thumb wheel 86 to position the emitter at a desired location relative to the target tissue region.

In addition, as shown in FIG. 16, the elongate body 82 that supports the radiant energy emitter 40 (e.g., an optical fiber assembly as shown in FIGS. 11-12 or the sheath for the electrical leads as shown in connection with FIGS. 9-10) can further include position indicia 92 on its surface to assist the clinician in placement of the ablation element within the instrument. The handle can further include a window 90 whereby the user can read the indicia (e.g., gradation markers) to gauge how far the emitter has been advanced into the instrument.

The assembly 32 can further include an endoscope translatory mechanism 98 as shown in FIG. 16 for controlled movement of the reflectance sensor or endoscope 76 within the instruments of the present invention. The exemplary positioner 98 can be incorporated into a handle 99 in the proximal region of the instrument, where the elongate body of the sensor 76 engages a thumb wheel 97 to control advancement and retraction of the emitter.

The apparatus of the present invention thus permits the selection of an ablative lesion, e.g., a circumferential lesion, of desired shape and size. This adjustability can be used advantageously to form a lesion at a desired location, or along a desired path, to effectively block conduction and thereby treat atrial fibrillation.

Although described in connection with cardiac ablation procedures, it should be clear that the instruments of the present invention can be used for a variety of other procedures where treatment with radiant energy is desirable, including laparoscopic, endoluminal, perivisceral, endoscopic, thoracoscopic, intra-articular and hybrid approaches.

The term "radiant energy" as used herein is intended to encompass energy sources that do not rely primarily on conductive or convective heat transfer. Such sources include, but are not limited to, acoustic and electromagnetic radiation sources and, more specifically, include microwave, x-ray, gamma-ray, ultrasonic and radiant light sources. The term "light" as used herein is intended to encompass electromagnetic radiation including, but not limited to, visible light, infrared and ultraviolet radiation.

The term "continuous" in the context of a lesion is intended to mean a lesion that substantially blocks electrical conduction between tissue segments on opposite sides of the lesion. The terms "circumferential" and/or "curvilinear," including derivatives thereof, are herein intended to mean a path or line which forms an outer border or perimeter that either partially or completely surrounds a region of tissue, or separate one region of tissue from another. Further, a "circumferential" path or element may include one or more of several shapes, and may be for example, circular, annular, oblong, ovular, elliptical, semi annular, or toroidal.

The term "lumen," including derivatives thereof, in the context of biological structures, is herein intended to mean any cavity or lumen within the body which is defined at least in part by a tissue wall. For example, cardiac chambers, the uterus, the regions of the gastrointestinal tract, the urinary tract, and the arterial or venous vessels are all considered illustrative examples of body spaces within the intended meaning.

The term "catheter" as used herein is intended to encompass any hollow instrument capable of penetrating body tissue or interstitial cavities and providing a conduit for selectively injecting a solution or gas, including without limitation, venous and arterial conduits of various sizes and shapes, bronchoscopes, endoscopes, cystoscopes, culpascopes, colonscopes, trocars, laparoscopes and the like. Catheters of the present invention can be constructed with biocompatible materials known to those skilled in the art such as those listed supra, e.g., silastic, polyethylene, Teflon, polyurethanes, etc. The term "lumen" including derivatives thereof, in the context of catheters is intended to encompass any passageway within a catheter instrument (and/or track otherwise joined to such instrument that can serve as a passageway) for the passage of other component instruments or fluids or for delivery of therapeutic agents or for sampling or otherwise detecting a condition at a remote region of the instrument. The term "catheter" is also intended to encompass any elongate body capable of serving as a conduit for one or more of the ablation, expandable or sensing elements described herein, e.g., energy emitters, balloons and/or endoscopes. Specifically in the context of coaxial instruments, the term "catheter" can encompass either the outer catheter body or sheath or other instruments that can be introduced through such a sheath. The use of the term "catheter" should not be construed as meaning only a single instrument but rather is used to encompass both singular and plural instruments, including coaxial, nested and other tandem arrangements.

The term "vessel" or "blood vessel" includes, without limitation, veins, arteries, and various chambers or regions of the heart, such as the atria, ventricles, coronary sinus, vena cava and, in particular, the ostia or antrum of the pulmonary veins.

It should be understood that the term "balloon" encompasses deformable hollow shapes which can be inflated into various configurations including balloon, circular, tear drop, etc., shapes dependent upon the requirements of the body cavity. Such balloon elements can be elastic or simply capable of unfolding or unwrapping into an expanded state. The balloon can further encompass multiple chamber configurations.

The term "transparent" is well recognized in the art and is intended to include those materials which allow transmission of energy through, for example, the primary balloon member. Preferred transparent materials do not significantly impede (e.g., result in losses of over 20 percent of energy transmitted) the energy being transferred from an energy emitter to the tissue or cell site. Suitable transparent materials include fluoropolymers, for example, fluorinated ethylene propylene (FEP), perfluoroalkoxy resin (PFA), polytetrafluoroethylene (PTFE), and ethylene-tetrafluoroethylene (ETFE) or polyester resins including polyethylene teraphathalate (PET).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A cardiac ablation instrument for treatment of atrial fibrillation comprising:
   a catheter adapted for disposition within a heart;
   an expandable balloon member coupled to the catheter and adapted for positioning proximate to a pulmonary vein;
   an ablation element within the balloon member for creating at least one lesion in the vicinity of the pulmonary vein; and
   a reflectance sensor for positioning the ablation element relative to the pulmonary vein,
   wherein the instrument further comprises at least one orientation marker detectable by the reflectance sensor, the orientation marker being configured to determine the angular position of the instrument relative to the pulmonary vein.

2. The instrument of claim 1, wherein the marker is located on the ablation element.

3. The instrument of claim 1, wherein the marker is on the expandable balloon of the instrument.

4. The instrument of claim 1, wherein the marker is detectable fluoroscopically.

5. The instrument of claim 1, wherein the orientation marker is adapted to be visualized together with an aiming beam.

6. The instrument of claim 1, wherein the orientation marker comprises a ring formed on the balloon, the ring adapted to facilitate dose selection.

7. The instrument of claim 1, wherein the orientation markers comprises multiple rings formed on the balloon, the rings adapted to facilitate dose selection.

8. A cardiac ablation instrument for treatment of atrial fibrillation comprising:
   a catheter adapted for disposition within a heart;
   an expandable balloon member coupled to the catheter and adapted for positioning proximate to a pulmonary vein, the expandable balloon having a tear-drop shape;
   an ablation element within the balloon member for creating at least one lesion in the vicinity of the pulmonary vein; and
   a reflectance sensor for positioning the ablation element relative to the pulmonary vein,
   wherein the reflectance sensor is capable of sensing contact between at least a portion of the instrument and cardiac tissue.

9. A cardiac ablation instrument for treatment of atrial fibrillation comprising:
   a catheter adapted for disposition within a heart;
   an expandable balloon member coupled to the catheter and adapted for positioning proximate to a pulmonary vein;
   an ablation element within the balloon member for creating at least one lesion in the vicinity of the pulmonary vein; and
   a reflectance sensor for positioning the ablation element,
   wherein the longitudinal position of the ablation element is adjustable relative to the balloon to create a lesion of variable size such that the ablation element can be configured to form a wide circumferential lesion by positioning the element at a rear location of the balloon member and the ablation element can be configured to form a smaller diameter circumferential lesion by positioning the ablation element closer to a front portion of the balloon.

10. The instrument of claim 1, wherein the ablation element is capable of axial movement such that it can be deployed at various positions to deliver ablative energy to a target tissue site.

11. The instrument of claim 1, wherein the ablation element is a radiant energy ablation element.

12. The instrument of claim 11, wherein the radiant energy ablation element is selected from the group consisting of microwave, x-ray, beta radiation, ionizing radiation, ultrasound, and light ablation elements.

13. The instrument of claim 12, wherein the radiant energy ablation element further comprises a light transmitting optical fiber adapted to receive radiant energy from a light source and a light emitting tip at a distal end of the fiber for emitting light.

14. The instrument of claim 12, wherein the ablation element comprises an ultrasound transducer.

15. The instrument of claim 12, wherein the ablation element comprises a microwave generator.

16. The instrument of claim 11, wherein the ablation element is adapted to project ablative energy forward.

17. The instrument of claim 11, wherein the expandable balloon member is adapted to clear a transmission pathway for radiant energy from the radiant energy ablation element to a target treatment site.

18. A cardiac ablation instrument for treatment of atrial fibrillation comprising:
a catheter adapted for disposition within a heart;
an expandable balloon member coupled to the catheter and adapted for positioning proximate to a pulmonary vein;
an ablation element within the balloon member for creating at least one lesion in the vicinity of the pulmonary vein; and
a reflectance sensor for positioning the ablation element relative to the pulmonary vein,
wherein the ablation element further comprises beam forming optics for projecting an annular beam of light, such that the ablation element projects at least a partial ring of ablative energy of variable diameter based on its axial position within the catheter body.

19. A cardiac ablation instrument for treatment of atrial fibrillation comprising:
a catheter adapted for disposition within a heart;
an expandable balloon member coupled to the catheter and adapted for positioning proximate to a pulmonary vein;
an ablation element within the balloon member for creating at least one lesion in the vicinity of the pulmonary vein; and
a reflectance sensor for positioning the ablation element relative to the pulmonary vein,
wherein the instrument further comprises an aiming beam generator to project a pattern of visible light coincident with a desired ablation location.

20. The instrument of claim 19, wherein the instrument further comprises at least one orientation marker that can be visualized together with the aiming beam.

21. A cardiac ablation instrument for treatment of atrial fibrillation comprising:
a catheter adapted for disposition within a heart;
an expandable balloon member coupled to the catheter and adapted for positioning proximate to a pulmonary vein;
an ablation element within the balloon member for creating at least one lesion in the vicinity of the pulmonary vein; and
a reflectance sensor for positioning the ablation element relative to the pulmonary vein,
wherein movement of the ablation element causes a change in size or fluence of an ablative energy beam incident on a target tissue.

22. A cardiac ablation instrument for treatment of atrial fibrillation comprising:
a catheter adapted for disposition within a heart;
an expandable balloon member coupled to the catheter and having a tear drop shape such that it is adapted for positioning proximate to a pulmonary vein;
an ablation element within the balloon member for creating at least one lesion in the vicinity of the pulmonary vein; and
a reflectance sensor for positioning the ablation element within the heart,
wherein the ablation element is capable of movement within the tear-drop shaped balloon and movement of the ablation element causes a change in size or fluence of an ablative energy beam incident on a target tissue.

23. The instrument of claim 22 wherein the instrument further comprises an aiming beam generator to project a pattern of visible light coincident with a desired ablation location.

24. The instrument of claim 22, wherein the instrument further comprises at least one orientation marker that can be visualized together with the aiming beam.

25. The instrument of claim 24, wherein the orientation marker further comprises at least one virtual orientation marker electronically generated on a display.

26. The instrument of claim 24, wherein the orientation marker comprises a ring formed on the tear-drop shaped balloon, the ring adapted to facilitate dose selection.

27. The instrument of claim 24, wherein the orientation marker comprises multiple rings formed on the tear-drop shaped balloon, the rings adapted to facilitate dose selection.

28. The instrument of claim 22, further including an illumination light source for the reflectance sensor.

29. The instrument of claim 22, wherein the ablation element serves as a radiant ablation element at high power and serves as an illumination light source for the reflectance sensor at low power.

* * * * *